United States Patent
Neumann

(10) Patent No.: US 10,832,822 B1
(45) Date of Patent: Nov. 10, 2020

(54) METHODS AND SYSTEMS FOR LOCATING THERAPEUTIC REMEDIES

(71) Applicant: KPN INNOVATIONS, LLC, Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 0 days.

(21) Appl. No.: 16/589,061

(22) Filed: Sep. 30, 2019

(51) Int. Cl.
*G16H 70/20* (2018.01)
*G06F 16/28* (2019.01)
*G16H 50/20* (2018.01)
*G16H 20/00* (2018.01)

(52) U.S. Cl.
CPC .......... *G16H 70/20* (2018.01); *G06F 16/285* (2019.01); *G16H 20/00* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 7,418,399 B2 | 8/2008 | Schaeffer et al. | |
| 7,880,751 B2* | 2/2011 | Kuo | A61C 7/00 345/634 |
| 7,899,764 B2 | 3/2011 | Martin et al. | |
| 8,095,384 B2 | 1/2012 | Firminger et al. | |
| 8,655,817 B2 | 2/2014 | Hasey et al. | |
| 8,838,513 B2* | 9/2014 | Sudharsan | G06N 7/005 706/25 |
| 9,460,400 B2 | 10/2016 | De Bruin et al. | |
| 10,073,951 B2 | 9/2018 | Mohebbi et al. | |
| 2010/0082367 A1* | 4/2010 | Hains | G06Q 50/22 705/2 |
| 2014/0046696 A1* | 2/2014 | Higgins | G16B 40/00 705/3 |
| 2018/0060494 A1* | 3/2018 | Dias | G16H 40/67 |

(Continued)

OTHER PUBLICATIONS

Chen et al.; "A Disease Diagnosis and Treatment Recommendation System Based on Big Data Mining and Cloud Computing"; Oct. 19, 2018; https://arxiv.org/pdf/1810.07762.pdf (Continued)

*Primary Examiner* — Michael Tomaszewski
(74) *Attorney, Agent, or Firm* — Caldwell Intellectual Propert

(57) ABSTRACT

A system for locating therapeutic remedies. The system includes a computing device that includes a k-means clustering module. The k-means clustering module is configured to receive at least a therapeutic constitutional inquiry, locate a user vibrancy record containing a plurality of user vibrancy datums, select at least a user vibrancy datum as a function of the at least a therapeutic constitutional inquiry, receive a clustering dataset that includes a plurality of unclassified cluster data entries, generate a k-means clustering algorithm using the clustering dataset, calculate a degree of similarity index value and select a classified data entry cluster. The system includes a k-nearest neighbors module that is configured to receive the selected classified data entry cluster, generate a k-nearest neighbors algorithm utilizing the selected classified data entry cluster, identify at least a therapeutic dataset, generate a therapeutic remedy instruction set, and display the therapeutic remedy instruction set on a graphical user interface.

18 Claims, 12 Drawing Sheets

(56) References Cited

U.S. PATENT DOCUMENTS

2019/0117978 A1* 4/2019 Arcot Desai ........ A61N 1/0534
2019/0139633 A1* 5/2019 Zhu ....................... G16H 80/00

OTHER PUBLICATIONS

Nezhad, Milad Zafar; "Data-Driven Modeling for Decision Support Systems and Treatment Management in Personalized Healthcare"; Jan. 1, 2018; https://digitalcommons.wayne.edu/cgi/viewcontent.cgi?article=3082&context=oa_dissertations.

McCallum et al.; "Efficient Clustering of High-Dimensional Data Sets With Appliation to Reference Matching"; 2000; http://citeseerx.ist.psu.edu/viewdoc/download? doi=10.1.1.561.9145&rep=rep1&type=pdf.

* cited by examiner

US 10,832,822 B1

METHODS AND SYSTEMS FOR LOCATING THERAPEUTIC REMEDIES

FIELD OF THE INVENTION

The present invention generally relates to the field of artificial intelligence. In particular, the present invention is directed to systems and methods for locating therapeutic remedies.

BACKGROUND

Locating therapeutic remedies that have been successful for individuals with shared medical conditions can be challenging. Therapeutic professionals are often overwhelmed with the quantity of literature to evaluate. Further, novel therapeutic remedies and medical conditions are created every day.

SUMMARY OF THE DISCLOSURE

In an aspect, a system for locating therapeutic remedies the system comprising at least a computing device wherein the at least a computing device further comprises one or more network interfaces; a non-volatile memory; and including one or more processors. The system includes a K-means clustering module operating on the at least a computing device, the k-means clustering module designed and configured to receive at least a therapeutic constitutional inquiry input from a graphical user interface by a therapeutic professional wherein the at least a therapeutic constitutional inquiry includes a user identifier; locate a user vibrancy record containing a plurality of user vibrancy datums stored in a vibrancy database as a function of the user identifier; select at least a user vibrancy datum as a function of the at least a therapeutic constitutional inquiry; receive a clustering dataset wherein the dataset further comprises a plurality of unclassified cluster data entries; generate a k-means clustering algorithm using the clustering dataset containing the plurality of cluster data entries containing unclassified data as input and wherein the k-means clustering algorithm outputs a definite number of classified data entry clusters wherein the data entry clusters each contain cluster data entries; calculate a degree of similarity index value wherein the degree of similarity index value further comprises a distance measurement between a classified data entry cluster and the at least a selected user vibrancy datum; and select a classified data entry cluster as a function of the degree of similarity index value. The system includes a K-nearest neighbors module operating on the at least a computing device the K-nearest neighbors module designed and configured to receive from the K-means clustering module the selected classified data entry cluster and the at least a therapeutic constitutional inquiry; generate a k-nearest neighbors algorithm utilizing the selected classified data entry cluster and the at least a therapeutic constitutional inquiry; identify at least a therapeutic dataset contained within the selected classified data entry cluster wherein the therapeutic dataset includes the at least a therapeutic constitutional inquiry and a therapeutic remedy; generate a therapeutic remedy instruction set as a function of identifying the therapeutic dataset; and display the therapeutic remedy instruction set on a graphical user interface located on the at least a computing device.

In an aspect, a method of locating therapeutic remedies the method comprising receiving by at least a computing device at least a therapeutic constitutional inquiry input from a graphical user interface by a therapeutic professional wherein the at least a therapeutic constitutional inquiry includes a user identifier. The method includes locating by the at least a computing device a user vibrancy record containing a plurality of user vibrancy datums stored in a vibrancy database as a function of the user identifier. The method includes selecting by the at least a computing device at least a user vibrancy datum as a function of the at least a therapeutic constitutional inquiry. The method includes receiving by the at least a computing device a clustering dataset wherein the dataset further comprises a plurality of unclassified cluster data entries. The method includes generating by the at least a computing device a k-means clustering algorithm using the clustering dataset containing the plurality of cluster data entries containing unclassified data as input and wherein the k-means clustering algorithm outputs a definite number of classified data entry clusters wherein the data entry clusters each contain cluster data entries. The method includes calculating by the at least a computing device a degree of similarity index value wherein the degree of similarity index value further comprises a distance measurement between a classified data entry cluster and the at least a selected user vibrancy datum. The method includes selecting by the at least a computing device a classified data entry cluster as a function of the degree of similarity index value. The method includes generating by the at least a computing device a k-nearest neighbors algorithm utilizing the selected classified data entry cluster and the at least a therapeutic constitutional inquiry. The method includes identifying by the at least a computing device at least a therapeutic dataset contained within the selected classified data entry cluster wherein the therapeutic dataset includes the at least a therapeutic constitutional inquiry and a therapeutic remedy. The method includes generating by the at least a computing device a therapeutic remedy instruction set as a function of identifying the therapeutic dataset. The method includes displaying by the at least a computing device the therapeutic remedy instruction set on a graphical user interface located on the at least a computing device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for locating therapeutic remedies. In an embodiment, a system for locating therapeutic remedies. The system includes a k-means clustering module that is configured to receive at least a therapeutic constitutional inquiry. The k-means clustering module is configured to locate a user vibrancy record containing a plurality of user vibrancy datums stored in a vibrancy database. The k-means clustering module is configured to select at least a user vibrancy datum as a function of at least a therapeutic constitutional inquiry. The k-means clustering module is configured to receive a clustering dataset containing a plurality of unclassified cluster data entries. The k-means clustering module is configured to generate a k-means clustering algorithm using the clustering dataset. The k-means clustering module is configured to calculate a degree of similarity index value that includes a distance measurement between a classified data entry cluster and a selected user vibrancy datum. The k-means clustering module is configured to select a classified data entry cluster as a function of the degree of similarity index value. The system includes a k-nearest neighbors module that is configured to generate a k-nearest neighbors algorithm utilizing the selected data entry cluster. The k-nearest neighbors module is configured to identify at least a therapeutic dataset contained within a selected classified data entry cluster. The k-nearest neighbors module is configured to generate a therapeutic remedy instruction set and display the therapeutic remedy instruction set on a graphical user interface.

Figure 1:
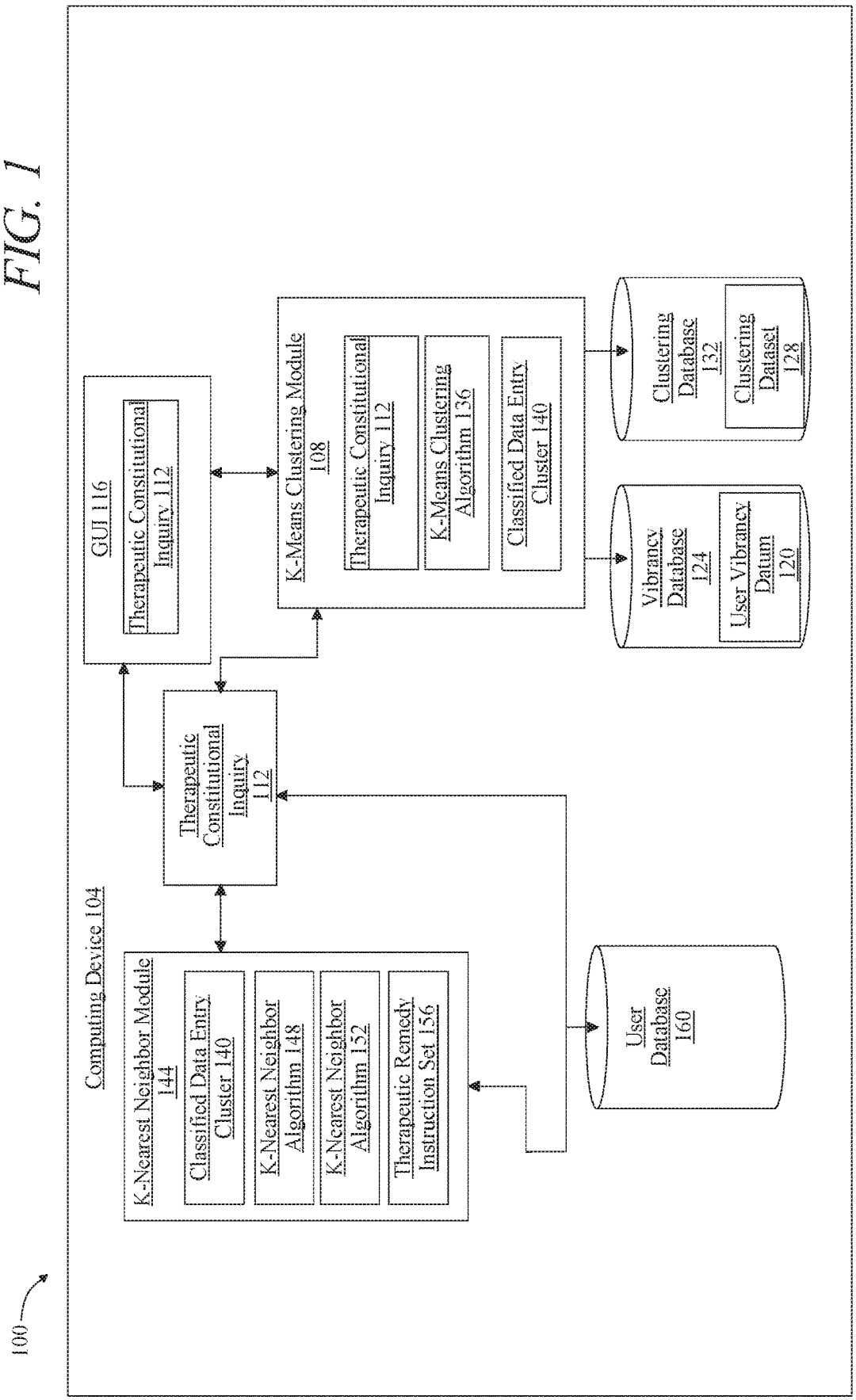
FIG. 1 is a block diagram illustrating an exemplary embodiment of a system for locating therapeutic remedies.

Referring now to FIG. 1, an exemplary embodiment of a system 100 for locating therapeutic remedies. System 100 includes at least a computing device 104, wherein the at least a computing device 104 further comprises one or more network interfaces, a non-volatile memory, and including one or more processors. Computing device 104, as used herein, includes any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include at least a server. At least a server may include a single computing device 104 operating independently or may include two or more computing device 104 operating in concert, in parallel, sequentially or the like; two or more computing device 104 may be included together in a single computing device 104 or in two or more computing device 104. At least a server may interact with one or more additional devices as described below in further detail via a network interface device. Network interface device may be utilized for connecting at least a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network may employ a wired and/or a wireless mode of communication. In general, any network topology may be used. Information (e.g., data, software etc.) may be communicated to and/or from a computer and/or a computing device 104. At least a server may include but is not limited to, for example, a computing device 104 or cluster of computing device 104 in a first location and a second computing device 104 or cluster of computing device 104 in a second location. At least a server may include one or more computing device 104 dedicated to data storage, security, distribution of traffic for load balancing, and the like. At least a server may distribute one or more computing tasks as described below across a plurality of computing device 104 of computing device 104, which may operate in parallel, in series, redundantly, or in any other manner used for distribution of tasks or memory between computing device 104. At least a server may be implemented using a "shared nothing" architecture in which data is cached at the worker, in an embodiment, this may enable scalability of system 100 and/or computing device 104.

With continued reference to FIG. 1, at least a computing device 104 may be designed and/or configured to perform any method, method step, or sequence of method steps in any embodiment described in this disclosure, in any order and with any degree of repetition. For instance, at least a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a k-means clustering module 108 operating on at least a computing device. K-means clustering module 108 may include any hardware and/or software module. K-means clustering module 108 is designed and configured to receive at least a therapeutic constitutional inquiry 112 from a graphical user interface 116 by a therapeutic professional wherein the at least a therapeutic constitutional inquiry 112 includes a user identifier; locate a user vibrancy record containing a plurality of user vibrancy datum 120 stored in a database as a function of the user identifier; select at least a user vibrancy datum 120 as a function of the at least a therapeutic constitutional inquiry 112; receive a clustering dataset 128 wherein the dataset further comprises a plurality of unclassified cluster data entries; generate a k-means clustering algorithm 136 using the clustering dataset 128 containing the plurality of cluster data entries containing unclassified data as input and wherein the k-means clustering algorithm 136 outputs a definite number of classified data entry cluster 140 wherein the data entry clusters each contain cluster data entries; calculate a degree of similarity index value wherein the degree of similarity index value further comprises a measurement distance between a data entry cluster and the at least a selected user vibrancy datum 120; and select a classified data entry cluster 140 as a function of the degree of similarity index value.

With continued reference to FIG. 1, k-means clustering module 108 is configured to receive at least a therapeutic constitutional inquiry 112 from a graphical user interface 116 by a therapeutic professional wherein the at least a therapeutic constitutional inquiry 112 includes a user identifier. A "therapeutic constitutional inquiry 112" as used in this disclosure, includes data describing a current diagnosed medical condition that a patient has been diagnosed with by a therapeutic professional. Medical condition may include a particular disease, one or more symptoms associated with a syndrome, a syndrome, and/or any other measure of current or future health and/or healthy aging. Conditions associated with therapeutic constitutional inquiry 112 may include, without limitation one or more diseases, defined for purposes herein as conditions that negatively affect structure and/or function of part or all of an organism. Conditions associated with therapeutic constitutional inquiry 112 may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Therapeutic constitutional inquiry 112 may be associated with one or more immune disorders, including without limitation immunodeficiencies and/or auto-immune conditions. Therapeutic constitutional inquiry 112 may be associated with one or more metabolic disorders. Therapeutic constitutional inquiry 112 may be associated with one or more endocrinal disorders. Therapeutic constitutional inquiry 112 may be associated with one or more cardiovascular disorders. Therapeutic constitutional inquiry 112 may be associated with one or more respiratory disorders. Therapeutic constitutional inquiry 112 may be associated with one or more disorders affecting connective tissue. Therapeutic constitutional inquiry 112 may be associated with one or more digestive disorders. Therapeutic constitutional inquiry 112 may be associated with one or more neurological disorders such as neuromuscular disorders, dementia, or the like. Therapeutic constitutional inquiry 112 may be associated with one or more disorders of the excretory system, including without limitation nephrological disorders. Therapeutic constitutional inquiry 112 may be associated with one or more liver disorders. Therapeutic constitutional inquiry 112 may be associated with one or more disorders of the bones such as osteoporosis. Therapeutic constitutional inquiry 112 may be associated with one or more disorders affecting joints, such as osteoarthritis, gout, and/or rheumatoid arthritis. Therapeutic constitutional inquiry 112 be associated with one or more cancers, including without limitation carcinomas, lymphomas, leukemias, germ cell tumor cancers, blastomas, and/or sarcomas. Therapeutic constitutional inquiry 112 may include descriptors of latent, dormant, and/or apparent disorders, diseases, and/or conditions. Therapeutic constitutional inquiry 112 may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with therapeutic constitutional inquiry 112 as described in this disclosure.

Still referring to FIG. 1, at least a therapeutic constitutional inquiry 112 may be stored in any suitable data and/or data type. For instance, and without limitation, at least a therapeutic constitutional inquiry 112 may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a therapeutic constitutional inquiry 112 may take; persons skilled in the art, upon reviewing the entirety of this disclosure, will be aware of various forms which may be suitable for use as at least a therapeutic constitutional inquiry 112 consistently with this disclosure.

With continued reference to FIG. 1, therapeutic constitutional inquiry 112 is input from a graphical user interface 116. Graphical user interface 116 may include without limitation, a form or other graphical element having data entry fields, wherein a therapeutic professional may enter a therapeutic constitutional inquiry 112. Graphical user interface 116 may include data entry fields that allow for a user to enter free form textual inputs describing a therapeutic constitutional inquiry 112. Graphical user interface 116 may provide drop-down lists, where users such as therapeutic professionals may be able to select one or more entries to indicate one or more therapeutic constitutional inquiries.

With continued reference to FIG. 1, therapeutic constitutional inquiry 112 is generated by a therapeutic professional. A "therapeutic professional" as used in this disclosure, includes a person who is licensed by a state and/or federal licensing agency that may help in identifying, preventing, and/or treating illness and/or disability. A therapeutic professional may include persons such as a functional medicine doctor, a doctor of osteopathy, a nurse practitioner, a physician assistant, a Doctor of Optometry, a doctor of dental medicine, a doctor of dental surgery, a naturopathic doctor, a doctor of physical therapy, a nurse, a doctor of chiropractic medicine, a doctor of oriental medicine, and the like. A therapeutic professional may include persons such as nurses, respiratory therapists, pharmacists, home health aides, audiologist, clinical nurse specialist, audiologist, nutritionist, dietician, clinical psychologists, psychiatric mental health nurse practitioners, and the like.

With continued reference to FIG. 1, therapeutic constitutional inquiry 112 input includes a user identifier. A "user identifier" as used in this disclosure, includes a unique identifier containing a series of numbers and/or letters that may uniquely identify a particular patient without disclosing a patient's name. For instance and without limitation, a user identifier may include a medical record number which may include a unique series of numbers that may be utilized to retrieve a patient's record.

With continued reference to FIG. 1, k-means clustering module 108 is configured to locate a user vibrancy record containing a plurality of user vibrancy datum 120 stored in a database as a function of the user identifier. A "user vibrancy record" as used in this disclosure, includes an electronic medical chart containing a complete record of a patient's key clinical data, medical history, lab results, vital signs, diagnoses, medications, treatment plans, progress notes, problems, immunization dates, allergies, radiology images, and the like. K-means clustering module 108 may locate a user vibrancy record by searching for a user identifier. In an embodiment, k-means clustering module 108 may match a user identifier contained within a therapeutic constitutional inquiry 112 to a user identifier contained within a user vibrancy record. User identifiers that are equivalent may belong to the same patient. User identifiers that are not equivalent may not belong to the same patient. User vibrancy record may contain a plurality of user vibrancy datum 120. A "user vibrancy datum 120" as used in this disclosure, includes data describing a component of a user vibrancy record. For instance and without limitation, a user vibrancy datum 120 may include all immunization records for a patient. In yet another non-limiting example, a user vibrancy datum 120 may be filtered to only contain immunization records for a patient during a specific time period of the patient's life or only for a particular immunization such as tetanus.

With continued reference to FIG. 1, system 100 may include a vibrancy database 124. Vibrancy database 124 may include any data structure for ordered storage and retrieval of data, which may be implemented as a hardware or software module. Vibrancy database 124 may be implemented, without limitation, as a relational database, a key-value retrieval datastore such as a NOSQL database, or any other format or structure for use as a datastore that a person skilled in the art would recognize as suitable upon review of the entirety of this disclosure. Vibrancy database 124 may include data entries as described in more detail below. K-means clustering module 108 selects at least a user vibrancy datum 120 as a function of at least a therapeutic constitutional inquiry 112. In an embodiment, therapeutic constitutional inquiry 112 may indicate which user vibrancy datum 120 is related to and/or relevant to a particular therapeutic constitutional inquiry 112. For instance and without limitation, a therapeutic constitutional inquiry 112 such as rheumatoid arthritis may be relevant to a user vibrancy datum 120 containing a lab work showing an elevate erythrocyte sedimentation rate (ESR). In yet another non-limiting example, a therapeutic constitutional inquiry 112 such as heart disease may be relevant to a genetic test showing confirming the presence of apolipoprotein E4 gene. In an embodiment, a therapeutic professional may indicate through a graphical user interface 116 what user vibrancy datum 120 may be relevant. In yet another embodiment, K-means clustering module 108 may determine which vibrancy datums may be relevant to a particular therapeutic constitutional inquiry 112 based on learned associations. K-means clustering module 108 may consult a list that may be stored within vibrancy database 124 that may list common associations between therapeutic constitutional inquiries and user vibrancy datum 120. K-means clustering module is configured to categorize at least a user vibrancy datum to a body location and select the at least a user vibrancy datum as a function of the body location. "Body location" as used in this disclosure includes a particular body part, body organ, muscle, tissue and/or body system impacted by a particular user vibrancy datum. For instance and without limitation, a headache may impact the frontal lobe of the head while endocarditis may impact heart muscle.

With continued reference to FIG. 1, K-means clustering module 108 is configured to receive a clustering dataset 128 wherein the clustering dataset 128 includes a plurality of unclassified cluster data entries. Dataset may be stored in any suitable data and/or data type. For instance and without limitation, dataset may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 1, dataset may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, datasets may be obtained from a plurality of sources. Datasets contained within clustering database 132 may contain a plurality of data entries, obtained for example, from patient medical records that have been stripped of identifying information. Datasets contained within body database may be obtained from patient surveys who may be sampled in a variety of methods such as by phone, mail, internet and the like. Patient surveys may be distributed to patients across a breadth of geographical locations and may also be stripped of identifying information. Datasets contained within clustering database 132 may be obtained from clinical data such as from facilities including nursing homes, hospitals, home health agencies, and the like.

With continued reference to FIG. 1, dataset may be stored in a clustering database 132. Clustering database 132 may include any database structure suitable for use as vibrancy database 124. Data entries contained within clustering dataset 128 include unclassified cluster data entries. "Unclassified cluster data entries" as used in this disclosure, include data entries that have not been assigned, generated, and/or calculated category labels. Classification may include the process of predicting a class of given data entries. Classification may include using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithms.

With continued reference to FIG. 1, K-means clustering module 108 is configured to generate a k-means clustering algorithm 136 using the clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. Cluster data entry may include data entries selected from a clustering dataset. Cluster data entry may be received from clustering database. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, k-means clustering module 108 generates a k-means clustering algorithm 136 containing unclassified data as input and outputs a definite number of classified data entry cluster 140 wherein the data entry clusters each contain cluster data entries. K-means clustering module 108 may select a specific number of groups or clusters to output, identified by the variable "k." Generating a k-means clustering algorithm 136 includes assigning inputs containing unclassified data to a "k-group" or "k-cluster" based on feature similarity. Centroids of k-groups or k-clusters may be utilized to generate classified data entry cluster 140. K-means clustering module 108 by select "k" variable by calculating k-means clustering algorithm 136 for a range of k values and comparing results.

K-means clustering module 108 may compared results across different values of k as the mean distance between cluster data entries and cluster centroid. K-means clustering module 108 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering module 108 may select a k value by classifying at least a therapeutic constitutional inquiry 112. K-means clustering module 108 may evaluate at least a therapeutic constitutional inquiry 112 to determine a constitutional classifier. A "constitutional classifier" as used in this disclosure, includes a label classifying a particular medical condition contained within a therapeutic constitutional inquiry to a particular disease classifier. A disease classifier may include classifying a medical condition by a particular classification system such as by body region or body system impacted by a medical condition, by anatomical classification such as by organ or tissue impacted by a particular medical condition, by etiological containing a cause for a particular medical condition, and/or by pathological containing a medical condition process. K-means clustering module 108 utilizes a constitutional classifier to select a definite number of classified data entry cluster 140 or k-value. In an embodiment, a particular constitutional classifier may indicate a preferred k-value based on previous data collections and calculations. For instance and without limitation, a constitutional classifier that indicates a body region such as the gastrointestinal system may be best suited for a k-value of 77 while a constitutional classifier that indicates a body region such as the left thumb may be best suited for a k-value of 14.

With continued reference to FIG. 1, generating a k-means clustering algorithm 136 includes generating initial estimates for k centroids which may be randomly generated or randomly selected from unclassified data input. K centroids may be utilized to define one or more clusters. K-means clustering module 108 may assign unclassified data to one or more k-centroids based on the squared Euclidean distance by first performing a data assigned step of unclassified data. K-means clustering module 108 may assign unclassified data to its nearest centroid based on the collection of centroids $c_i$ of centroids in set C. Unclassified data may be assigned to a cluster based on $\text{argmin}_{c_i} \ni {}_C \text{dist}(c_i, x)^2$, where argmin includes argument of the minimum; ci includes a collection of centroids in a set C; and dist includes standard Euclidean distance. K-means clustering module 108 may then recompute centroids by taking mean of all cluster data entries assigned to a centroid's cluster. This may be calculated based on $ci=1/|Si|\Sigma xi \in Si^{xi}$. K-means clustering module 108 may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering module 108 is configured to calculate a degree of similarity index value. A "degree of similarity index value" as used in this disclosure, includes a distance measurement indicating a measurement between each data entry cluster generated by k-means clustering algorithm 136 and a selected user vibrancy datum 120. Degree of similarity index value may indicate how close a particular user vibrancy datum 120 is to being classified by k-means algorithm to a particular cluster. K-means clustering module 108 may evaluate the distances of the user vibrancy datum 120 to the k-number of clusters output by k-means clustering algorithm 136. Short distances between a user vibrancy datum 120 and a cluster may indicate a higher degree of similarity between a user vibrancy datum 120 and a particular cluster. Longer distances between a user vibrancy datum 120 and a cluster may indicate a lower degree of similarity between a user vibrancy datum 120 and a particular cluster. Degree of similarity index value may include calculating by k-means clustering module 108 a background factor multiplied by an age factor and a vibrancy factor and divided by a life value factor. A "background factor" as used in this disclosure, includes a numerical value indicating how similar background demographic details may be between demographic background information regarding a user and demographic background information pertaining to cluster data entries contained within a particular cluster. Demographic background information may include information relating to address, marital status, sex, race, religion, occupation, offspring, and the like. An "age factor" as used in this disclosure, includes a numerical value indicating how similar in age a user may be as compared to cluster data entries contained within a particular cluster. Age may include the length of time that a user has lived since being born. A "vibrancy factor" as used in this disclosure, includes a numerical value indicating how similar a user's medical condition may be as compared to cluster data entries contained within a particular cluster. Medical condition may include any of the medical conditions contained within a therapeutic constitutional inquiry 112 as described above. Vibrancy factor may include a disease score multiplied by a life year score. Disease score may include a numerical value indicating how severe a particular disease is. In an embodiment, a higher disease score may indicate a more severe disease. Life year score may include a numerical value indicating an estimated number of years that a user has left to live before succumbing to death. A "life value factor" as used in this disclosure, includes a numerical measurement indicating how similar traits may be between a user and cluster data entries contained within a particular cluster. Traits may include ethical and/or moral values of importance that a user may choose to encompass as part of their lifestyle. Traits may include for example authenticity, compassion, community, curiosity, friendship, generosity, honesty, kindness, knowledge, leadership, love, responsibility, security, self-respect, spirituality, stability, and/or wisdom. In an embodiment, a user may indicate the top 3-5 traits that are more important to a user.

With continued reference to FIG. 1, k-means clustering module 108 selects a classified data entry cluster 140 as a function of the degree of similarity index value. In an embodiment, k-means clustering module 108 may select a classified data entry cluster 140 with the smallest degree of similarity index value indicating a high degree of similarity between a user vibrancy datum 120 and a particular data entry cluster. In an embodiment, k-means clustering module 108 may not select a classified data entry cluster 140 with the largest degree of similarity index value indicating a low degree of similarity between a user vibrancy datum 120 and a particular data entry cluster.

With continued reference to FIG. 1, system 100 includes a k-nearest neighbors module 144 operating on at least a computing device. K-nearest neighbors module 144 may include any hardware and/or software module. K-nearest neighbors module 144 is designed and configured to receive from the K-means clustering module 108 the selected classified data entry cluster 140 and the at least a therapeutic constitutional inquiry 112; generate a k-nearest neighbors algorithm utilizing the selected classified data entry cluster 140 and the at least a therapeutic constitutional inquiry 112; identify a therapeutic dataset contained within the selected classified data entry cluster 140 wherein the selected classified data entry includes the at least a therapeutic constitutional inquiry 112 and a therapeutic remedy; generate a therapeutic remedy instruction set 156 as a function of identifying the therapeutic dataset; and display the therapeutic remedy instruction set 156 on a graphical user interface 116 located on the at least a computing device.

With continued reference to FIG. 1, k-nearest neighbors module 144 is configured to receive from k-means clustering module 108 the selected classified data entry cluster 140 and the at least a therapeutic constitutional inquiry 112. K-nearest neighbors module 144 may receive from k-means clustering module 108 selected classified data entry cluster 140 and the at least a therapeutic constitutional inquiry 112 utilizing any network topography as described herein. Selected classified data entry cluster 140 may be utilized by k-nearest neighbors module 144 as training data to generate a k-nearest neighbors algorithm 152 as described in more detail below. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like;

categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a computing device and/or k-nearest neighbors module 144 may correlate any input data as described in this disclosure to any output data as described in this disclosure.

With continued reference to FIG. 1, k-nearest neighbors module 144 generates a k-nearest neighbors algorithm 152 utilizing the selected classified data entry cluster 140 and the at least a therapeutic constitutional inquiry 112. "K-nearest neighbors algorithm" as used in this disclosure, includes a lazy-learning method that utilizes feature similarity to analyze how closely out-of-sample-features resemble training data to locate possible optimal vector outputs, classify possible optimal vector outputs, calculate an optimal vector output and generate an optimal vector output. Optimal vector outputs may include vector outputs that may generate a desired outcome that satisfies a k-nearest neighbors algorithm. Calculating an optimal vector output utilizing a k-nearest neighbors algorithm 152 may include specifying a K-value, selecting k entries in a database which are closest to the known sample, determining the most common classifier of the entries in the database, and classifying the known sample. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, generating k-nearest neighbors algorithm 152 includes generating a first vector output containing a data entry cluster, generating a second vector output containing at least a therapeutic constitutional inquiry 112 and calculate the distance between the first vector output and the second vector output using Euclidean distance measurement. A first vector output is n n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of priorities, and/or is to be compared to such a weighing of priorities. Priorities may be generated based on user input, where a user may prefer a particular attribute.

With continued reference to FIG. 1, generating k-nearest neighbors module 144 generates an optimal vector output as a function of the distance between the first vector output containing a data entry cluster and the second vector output containing the at least a therapeutic constitutional inquiry 112. K-nearest neighbors module 144 identifies a therapeutic dataset utilizing the optimal vector output.

With continued reference to FIG. 1, k-nearest neighbors module 144 identifies at least a therapeutic dataset contained within the selected classified data entry cluster 140. A "therapeutic dataset" as used in this disclosure, includes the at least a therapeutic constitutional inquiry 112 and a correlated therapeutic remedy. A therapeutic constitutional inquiry may be correlated to a therapeutic remedy by a shared trait whereby a therapeutic remedy may be utilized as a form of treatment for a therapeutic constitutional inquiry. For example, a therapeutic constitutional inquiry such as a headache may be correlated to a therapeutic remedy such as aspirin. In yet another non-limiting example, a therapeutic constitutional inquiry such as heartburn may be correlated to a therapeutic remedy such as an antacid. A "therapeutic remedy" as used in this disclosure, includes any data that identifies a process that improves a current, incipient, or probable future medical condition affecting a person contained within a therapeutic constitutional inquiry 112. Prescriptive processes may include, without limitation, dietary or nutritional recommendations based on data including nutritional content, digestibility, or the like. Prescriptive processes may include one or more medical procedures. Prescriptive processes may include one or more physical, psychological, or other therapies. Prescriptive processes may include one or more medications, supplements, homeopathic remedies, herbs, therapies, and the like. For instance and without limitation, a therapeutic remedy may include a combination of supplements that may be utilized to treat a user with a medical condition such as Lyme Disease. In yet another non-limiting example, a therapeutic remedy may include a prescription medication that may be utilized to treat a user with a medication condition such as cystic fibrosis.

With continued reference to FIG. 1, k-nearest neighbors module 144 is configured to generate a therapeutic remedy instruction set 156 as a function of identifying a therapeutic dataset. A 'therapeutic remedy instruction set 156" as used in this disclosure, includes data identifying one or more therapeutic remedies selected from one or more therapeutic datasets that have been utilized to treat the same therapeutic constitutional inquiry 112. For instance and without limitation, k-nearest neighbors module 144 may identify three therapeutic datasets by generating k-nearest neighbors algorithm 152 utilizing the selected classified data entry cluster 140. In such an instance, three therapeutic datasets may include a first therapeutic dataset containing a therapeutic constitutional inquiry 112 such as type two diabetes mellitus and a first therapeutic remedy such as metformin; a second therapeutic dataset containing the same therapeutic constitutional inquiry 112 of type two diabetes mellitus and a second therapeutic remedy such as cinnamon bark capsules and chromium picolinate; and a third therapeutic dataset containing the same therapeutic constitutional inquiry 112 of type two diabetes mellitus and a third therapeutic remedy such as *ginseng*.

With continued reference to FIG. 1, k-nearest neighbors module 144 is configured to display a therapeutic remedy instruction set 156 on a graphical user interface 116 located on at least a computing device. Graphical user interface 116 may include any of the graphical user interface 116 as described above.

Figure 2:
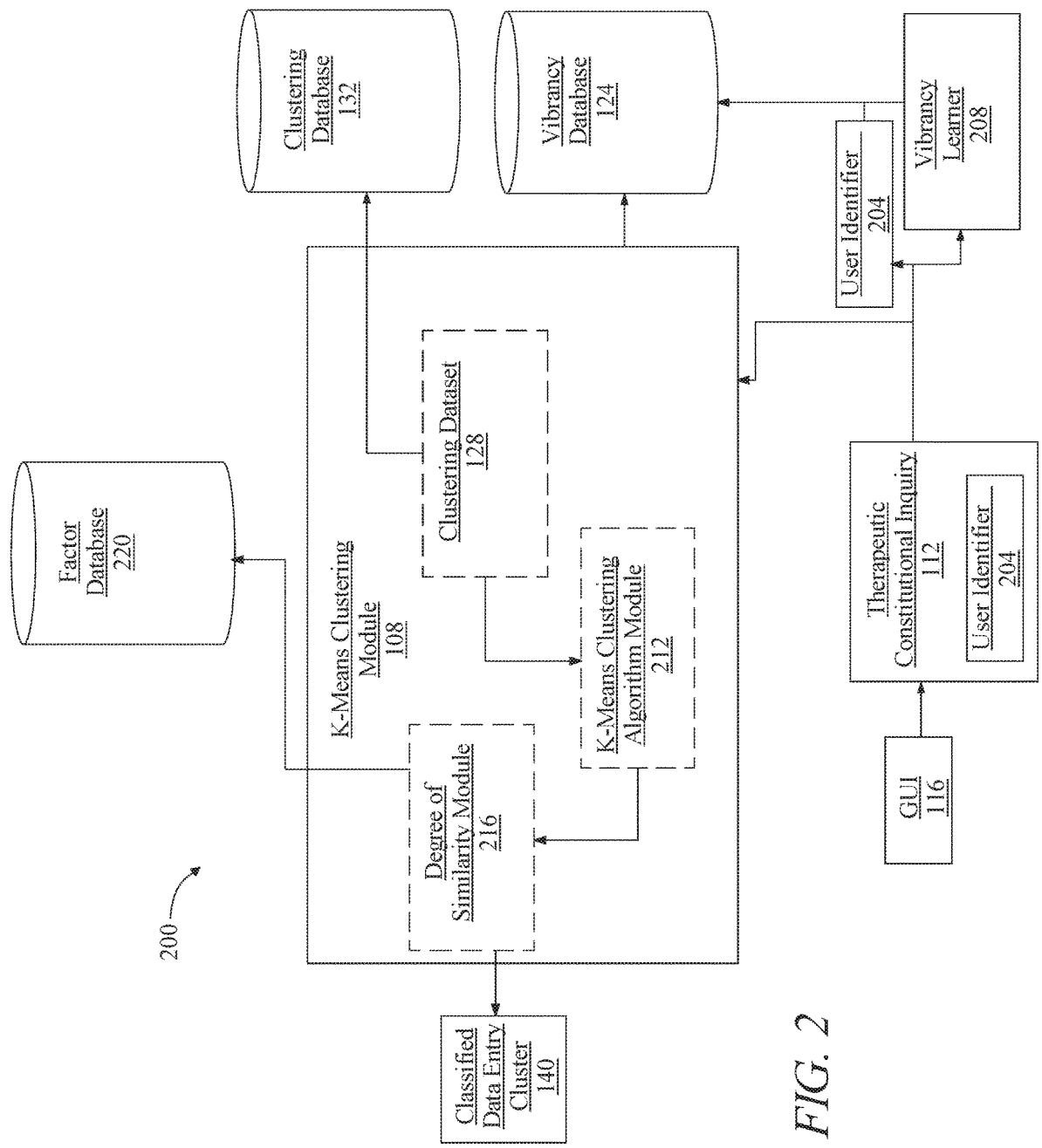
FIG. 2 is a block diagram illustrating an exemplary embodiment of a k-means clustering algorithm.

Referring now to FIG. 2, an exemplary embodiment 200 of k-means clustering module 108 is illustrated. K-means clustering module 108 receives at least a therapeutic constitutional inquiry 112 input from a graphical user interface 116 by a therapeutic professional. Therapeutic constitutional inquiry 112 input includes any of the therapeutic constitutional inputs as described above in reference to FIG. 1. For instance and without limitation, therapeutic constitutional inquiry 112 input may include a current diagnosed medical condition that a user may have been diagnosed with such as Alzheimer's disease. In yet another non-limiting example, therapeutic constitutional input may include a current diagnosis such as methane positive small intestinal bacterial overgrowth. Therapeutic constitutional inquiry 112 includes a user identifier 204. User identifier 204 may include any of the user identifiers as described above in reference to FIG. 1. User identifier may be utilized by k-means clustering module 108 to locate a user vibrancy record within vibrancy database 124.

With continued reference to FIG. 2, vibrancy database 124 may include any database structure as described above in reference to FIG. 1. Vibrancy database 124 may include data entries regarding a user's medical profile as described above in more detail in reference to FIG. 1. Vibrancy database 124 may include for example, medical record data including immunization records, lab results, clinical notes and the like as described above in more detail in reference to FIG. 1. K-means clustering module 108 locates a user vibrancy record containing a plurality of user vibrancy datum 120 stored in a vibrancy database 124 as a function of the user identifier. K-means clustering module 108 may verify a user vibrancy record by comparing the user identifier received with a therapeutic constitutional inquiry 112 to a user identifier stored in a user vibrancy record. K-means clustering module 108 may verify a user identifier when the user identifier received with a therapeutic constitutional inquiry 112 matches a user identifier stored in a user vibrancy record. K-means clustering module 108 may not verify a user identifier when the user identifier received with a therapeutic constitutional inquiry 112 does not match a user identifier stored in a user vibrancy record. In an embodiment, k-means clustering module 108 may verify a user identifier such as using cryptographic means including comparing a hash, using a public/private key pair, and the like.

With continued reference to FIG. 2, k-means clustering module 108 may include a vibrancy learner 208 that may select at least a user vibrancy datum 120 as a function of the at least a therapeutic constitutional inquiry 112. Vibrancy learner 208 may include any hardware and/or software module. Vibrancy learner 208 may be configured to select a user vibrancy datum 120 related to a therapeutic constitutional inquiry 112 using machine-learning processes. For instance and without limitation, vibrancy learner 208 may be configured to select a user vibrancy datum 120 that includes a lab test showing a genetic mutation to the LCT gene responsible for the production of the enzyme lactase to a therapeutic constitutional inquiry 112 that includes a medical condition of lactose intolerance. In yet another non-limiting example, vibrancy learner 208 may be configured to select a user vibrancy datum 120 that includes a medical progress notes that show progressive worsening of a user's symptoms over a six month span related to a therapeutic constitutional inquiry 112 containing a diagnosis of multiple sclerosis. A machine-learning process is a process that automatedly uses a body of data known as "training data" and/or a "training set" to generate an algorithm that will be performed by a computing device and/or module to produce outputs given data provided as inputs; this is in contrast to a non-machine-learning software program where the commands to be executed are determined in advance by a user and written in a programming language.

Still referring to FIG. 2, vibrancy learner 208 may be designed and configured to select at least a user vibrancy datum 120 by creating a machine-learning model relating therapeutic constitutional inquiries to user vibrancy datum 120 using a training set and selecting a user vibrancy datum 120 using the machine-learning model; at least a machine-learning model may include one or more models that determine a mathematical relationship between therapeutic constitutional inquiries and user vibrancy datum 120. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 2, machine-learning algorithm used to generate machine-learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 2, K-means clustering module 108 receives a clustering dataset 128. K-means clustering module 108 may receive clustering dataset 128 from clustering database 132. Clustering database 132 may include any data structure suitable for use as vibrancy database 124. Clustering database 132 may include clustering dataset 128 that include a plurality of unclassified cluster data entries. Clustering dataset 128 may be obtained from medical records and charts as well as from expert inputs as described above in reference to FIG. 1. Clustering dataset 128 may be organized within clustering dataset 128 according to common shared characteristics. For instance and without limitation, clustering dataset 128 may be organized according to shared traits of cluster data entries contained within clustering dataset 128 such as clustering dataset 128 that contain cluster data entries from users who are between the ages of 45-55 years old or cluster data entries from users who have all been diagnosed with Lupus. Organization of clustering dataset 128 is described below in more detail.

With continued reference to FIG. 2, k-means clustering module 108 may include k-means clustering algorithm 136 module 212. K-means clustering algorithm 136 module 212 may include any hardware and/or software module. K-means clustering algorithm 136 module 212 generates k-means clustering algorithm 136 using the clustering dataset 128 received from clustering database 132. K-means clustering algorithm 136 module 212 receives clustering dataset 128 as input and outputs a definite number of classified data entry cluster 140 that each contain cluster data entries. K-means clustering algorithm 136 module 212 may determine k-value that will set a fixed number of classified data entry cluster 140 as outputs utilizing any of the methods as described above in reference to FIG. 1. In an embodiment, k-value may be selected based generating k-means clustering algorithm 136 repeatedly until a k-value is averaged and selected. In yet another non-limiting example, a k-value may be selected based on a particular clustering dataset 128 that may be best suited for a particular k-value. K-means clustering algorithm 136 module receives as input unclassified clustering dataset 128. Unclassified clustering dataset 128 may include any of the unclassified clustering dataset 128 as described above in reference to FIG. 1. K-means clustering algorithm 136 module outputs classified data entry cluster 140. Data entry clusters may be classified by k-means clustering algorithm 136 module using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithms. K-means clustering algorithm 136 module may generate a soft k-means clustering algorithm 136 wherein a "soft k-means clustering algorithm" as used in this disclosure includes a k-means clustering algorithm where a cluster data entry may be selected and/or assigned to multiple clusters of the definite number of classified data entry cluster 140. For instance and without limitation, k-means clustering algorithm 136 module may generate a soft k-means clustering algorithm 136 that has a k-value of seven and where a particular cluster data entry may be selected and assigned to three of the seven classified data entry cluster 140. K-means clustering algorithm module may generate a hard k-means clustering algorithm 136 wherein a "hard k-means clustering algorithm" as used in this disclosure includes a k-means clustering algorithm where a cluster data entry may be selected to be assigned to one cluster of the definite number of classified data entry cluster. For instance and without limitation, k-means clustering algorithm 136 module may generate a hard k-means clustering algorithm 136 that has a k-value of seven and where a particular cluster data entry may be selected and assigned to one of the seven classified data entry cluster 140. K-means clustering algorithm 136 module may select a hard k-means algorithm and/or a soft k-means algorithm based on expert input as described in more detail below. In an embodiment, k-means clustering algorithm 136 module may select a hard k-means algorithm and/or a soft k-means algorithm based on learned associations between clustering dataset 128 and classified data entry outputs such as by learned associations such as from vibrancy learner 208.

With continued reference to FIG. 2, k-means clustering module 108 may include degree of similarity module 216.

Degree of similarity module 216 may include any hardware and/or software module. Degree of similarity module 216 may calculate a degree of similarity index value that contains a distance measurement between a data entry cluster and a user vibrancy datum 120. Degree of similarity index value may include any of the degree of similarity index values as described above in reference to FIG. 1. Degree of similarity index value may include a background factor multiplied by an age factor and a vibrancy factor and divided by a life value factor. Factors utilized to calculate degree of similarity index value may be included in factor database 220. Factor database 220 may include any data structure suitable for use as vibrancy database 124 as described in more detail below.

With continued reference to FIG. 2, degree of similarity module may evaluate degree of similarity index value for a particular classified data entry cluster 140 and select a classified data entry cluster 140 as a function of the degree of similarity index value. In an embodiment degree of similarity module may select a classified data entry cluster 140 that is the most similar to user vibrancy datum 120. In an embodiment, classified data entry cluster 140 that contains the smallest numerical score for the similarity index value may indicate the most similar classified data entry cluster 140 to a selected user vibrancy datum 120. Similarity index value module may be configured to calculate and evaluate similarity index values.

Figure 3:
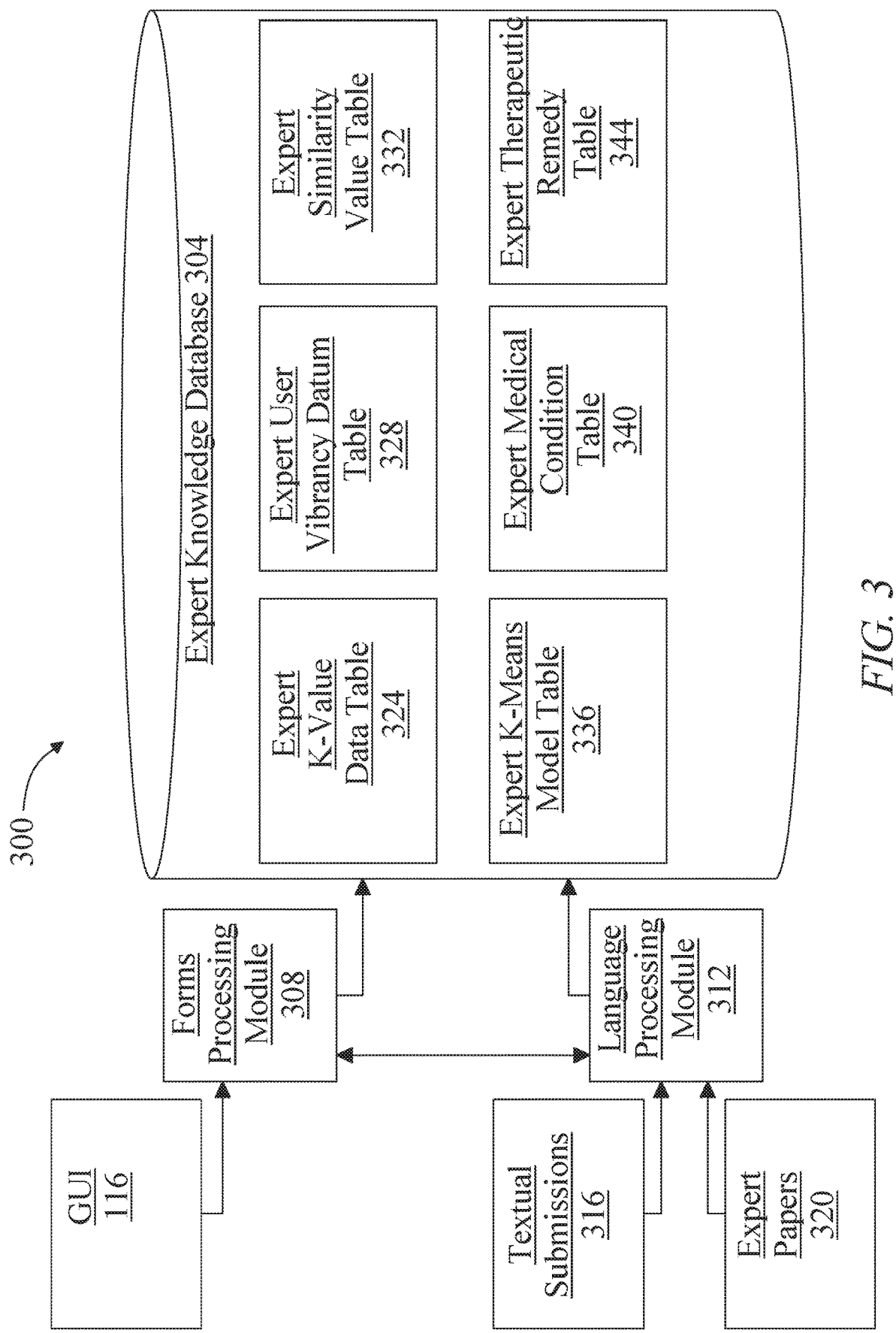
FIG. 3 is a block diagram of an exemplary embodiment of an expert knowledge database.

Referring now to FIG. 3, an exemplary embodiment 300 of expert knowledge database 304 is illustrate. Expert knowledge database may include any data structure and/or data store suitable for use as vibrancy database 124 as described above. One or more database tables may be linked to one another by, for instance, common column values. For instance, a common column between two tables of expert knowledge database may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 3, expert knowledge database includes a forms processing module 308 that may sort data entered in a submission via graphical user interface 116 by, for instance, sorting data from entries in the graphical user interface 116 to related categories of data; for instance, data entered in an entry relating in the graphical user interface 116 to a medical condition may be sorted into variables and/or data structures for storage of medical conditions, while data entered in an entry relating to a category of vibrancy datum and/or an element thereof may be sorted into variables and/or data structures for the storage of, respectively, categories of vibrancy datums. Where data is chosen by an expert from pre-selected entries such as drop-down lists, data may be stored directly; where data is entered in textual form, language processing module 312 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 312 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 316, such as accomplished by filling out a paper or PDF form and/or submitting narrative information, may likewise be processed using language processing module 312. Data may be extracted from expert papers 320, which may include without limitation publications in medical and/or scientific journals, by language processing module 312 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 3, one or more tables contained within expert knowledge database may include expert k-value data table 324; expert k-value data table 324 may include one or more data entries describing expert input regarding k-values for clustering dataset 128 and/or therapeutic constitutional inquiries. One or more tables contained within expert knowledge database may include expert user vibrancy datum 120 table 328; expert user vibrancy datum 120 table 328 may include one or more data entries describing expert input regarding therapeutic constitutional inquiries and related user vibrancy datum 120. One or more tables contained within expert knowledge database may include expert similarity value table 332; expert similarity value table 332 may include one or more data entries describing expert similarity values and/or calculations. One or more tables contained within expert knowledge database may include expert k-means model table 336; expert k-means model table 336 may include one or more data entries describing expert input regarding calculations of k-means model. One or more tables contained within expert knowledge database may include expert medical condition table 340; expert medical condition table 340 may include one or more data entries describing expert input regarding medical conditions. One or more tables contained within expert knowledge database may include expert therapeutic remedy table 344; expert therapeutic remedy table 344 may include one or more data entries describing expert therapeutic remedies.

Figure 4:
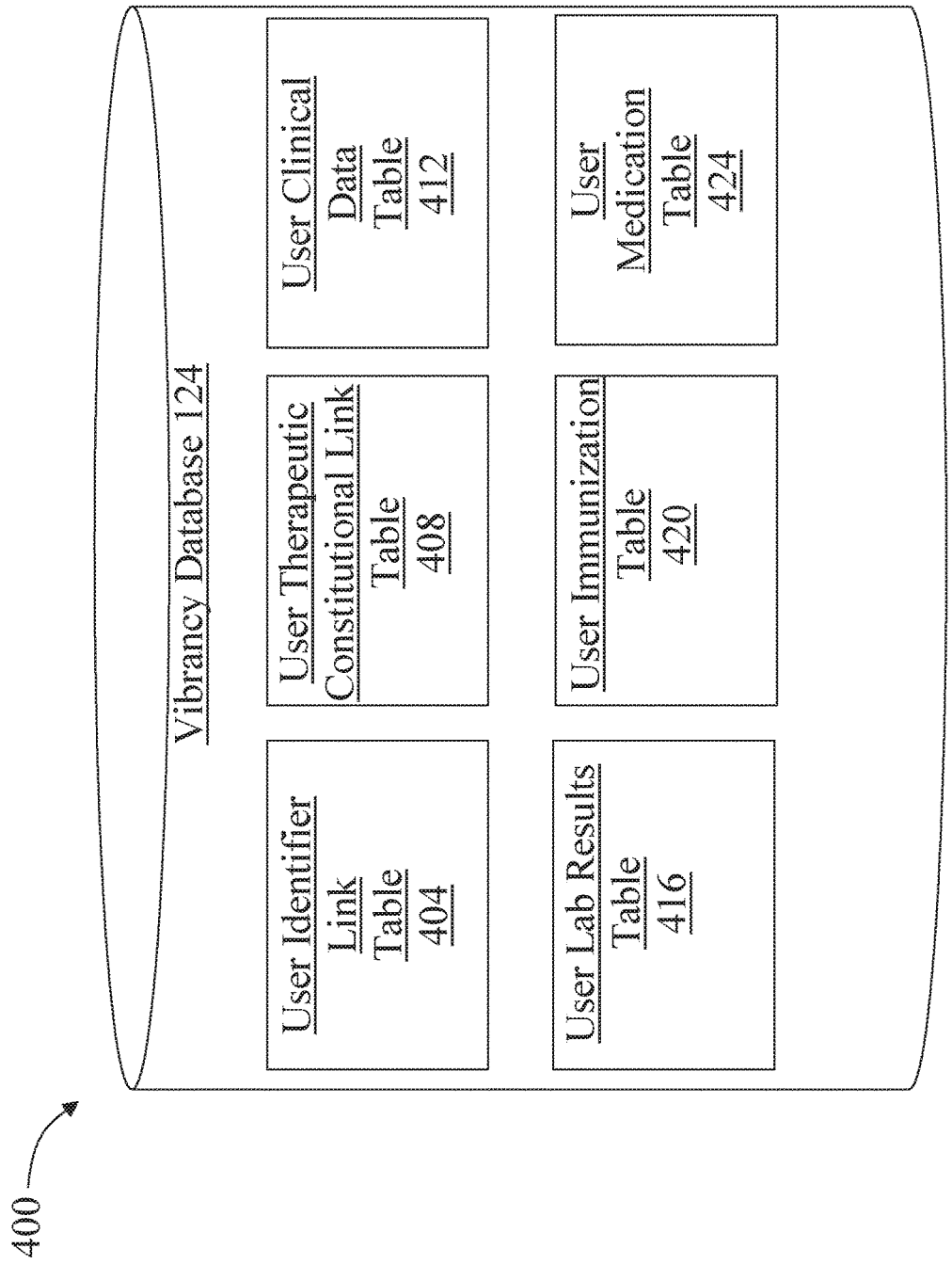
FIG. 4 is a block diagram illustrating an exemplary embodiment of a vibrancy database.

Referring now to FIG. 4, an exemplary embodiment of vibrancy database 124 is illustrated. Vibrancy database 124 may include any data structure as described above in reference to FIG. 1. One or more tables contained within vibrancy database 124 may include user identifier link table 404; user identifier link table 404 may include information describing a user identifier. For instance and without limitation, user identifier link table may include data entries containing a list of users and associated user identifiers that may be utilized to verify a user identifier as compared to a user identifier contained within a therapeutic constitutional inquiry 112. One or more tables contained within vibrancy database 124 may include user therapeutic constitutional link table 408; user therapeutic constitutional link table 408 may include one or more data entries containing a user therapeutic constitutional inquiry 112 linked to a user vibrancy datum 120. For instance and without limitation, user therapeutic constitutional link table 408 may include a therapeutic constitutional inquiry 112 such as type two diabetes mellitus linked to a user vibrancy datum 120 such as a fasting hemoglobin A1C. One or more tables contained within vibrancy database 124 may include user clinical data table 412; user clinical data table 412 may include one or more data entries containing user clinical data. For instance and without limitation, user clinical data table 412 may include one or more data entries describing the health status of a user over a specific period of time. One or more tables contained within vibrancy database 124 may include user lab results table 416; user lab results table 416 may include one or more data entries containing user lab results. For instance and without limitation, user lab results table 416 may include one or more user label results such as a blood sample analyzed as part of a chem-7 panel, or a hair sample analyzed for a particular genetic mutation. One or more tables contained within vibrancy database 124 may include user immunization table 420; user immunization table 420 may include one or more data entries describing the immunization records of a user. For instance and without limitation, user immunization table 420 may include data describing the date a user received a tetanus immunization, along with information describing the dose, location where administered, as well as the lot number and manufacturer of the tetanus immunization. One or more tables contained within vibrancy database 124 may include user medication table 424; user medication table 424 may include one or more data entries describing the medication history a user. For instance and without limitation, user medication table 424 may include data describing medications that a user consumed over a particular period of time. User medication table 424 may include information regarding both prescription medication and nonprescription medications including over the counter medications, supplements, herbals, nutraceuticals, homeopathic remedies, and the like.

Figure 5:
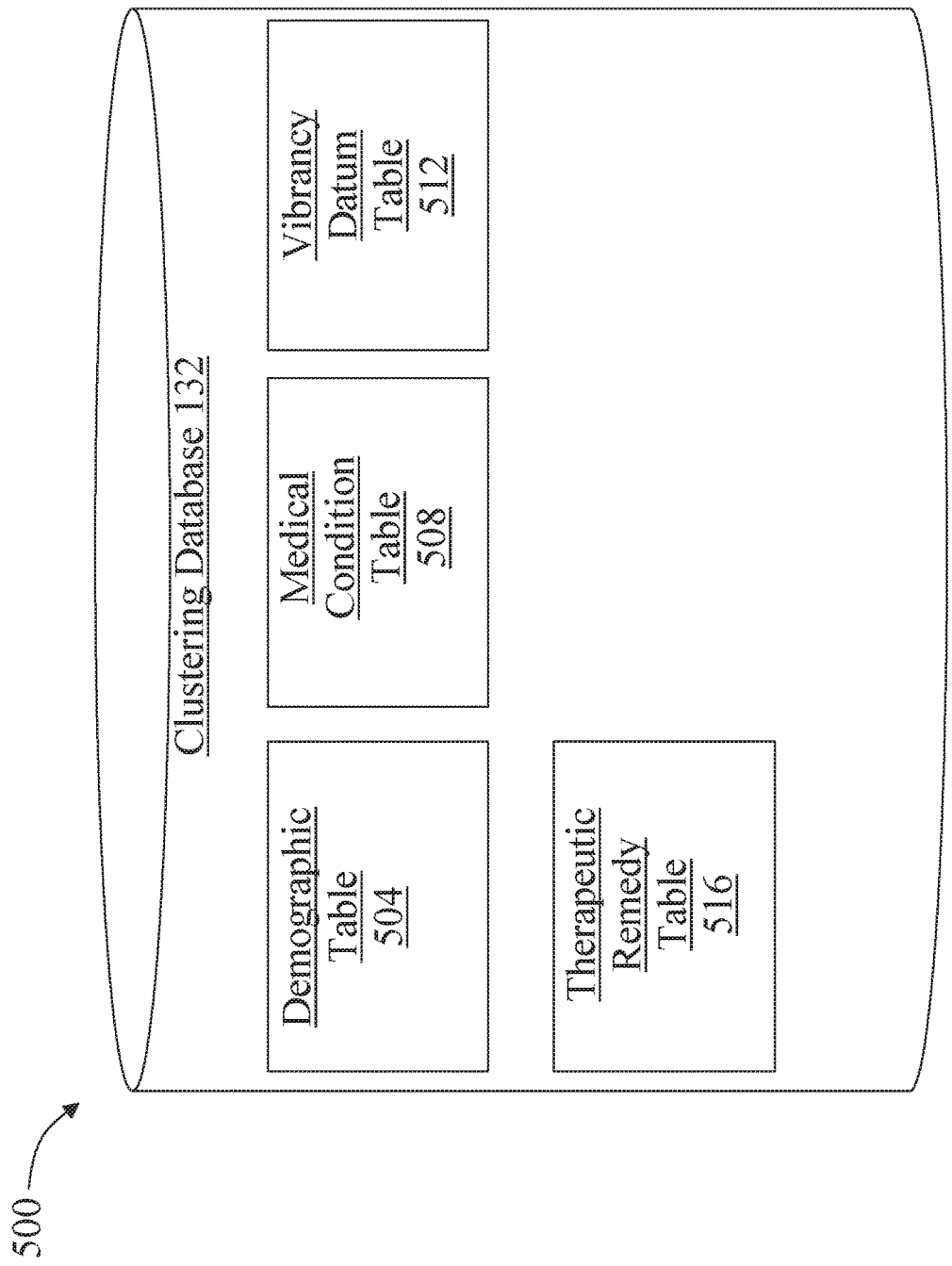
FIG. 5 is a block diagram illustrating an exemplary embodiment of a clustering database.

Referring now to FIG. 5, an exemplary embodiment of clustering database 132 is illustrated. Clustering database 132 may include any data structure suitable for use as vibrancy database 124. One or more tables contained within clustering database 132 may include demographic table 504; demographic table may include one or more clustering dataset 128 organized by demographics. For instance and without limitation, demographic table 504 may include one or more clustering dataset 128 organized by age, race, occupation, income, and the like. One or more tables contained within clustering database 132 may include medical condition table 508; medical condition table 508 may include one or more clustering dataset 128 organized by medical condition. For instance and without limitation, medical condition table 508 may include one or more clustering dataset 128 organized by medical condition such as lupus, multiple sclerosis, type one diabetes mellitus, hypothyroidism, and the like. One or more tables contained within clustering database 132 may include vibrancy datum table 512; vibrancy datum table 512 may include one or more clustering dataset 128 organized by vibrancy datum. For instance and without limitation, vibrancy datum table may include one or more clustering dataset 128 organized by lab result, tissue sample, clinical note, medication, and the like. One or more tables contained within clustering database 132 may include therapeutic remedy table 516; therapeutic remedy table 516 may include one or more clustering dataset 128 organized by therapeutic remedy. For instance and without limitation, therapeutic remedy table 516 may include one or more clustering dataset 128 organized by a particular therapeutic remedy including for example medication name, medication dose, supplement name, meditation sequence, prayer sequence, and the like.

Figure 6:
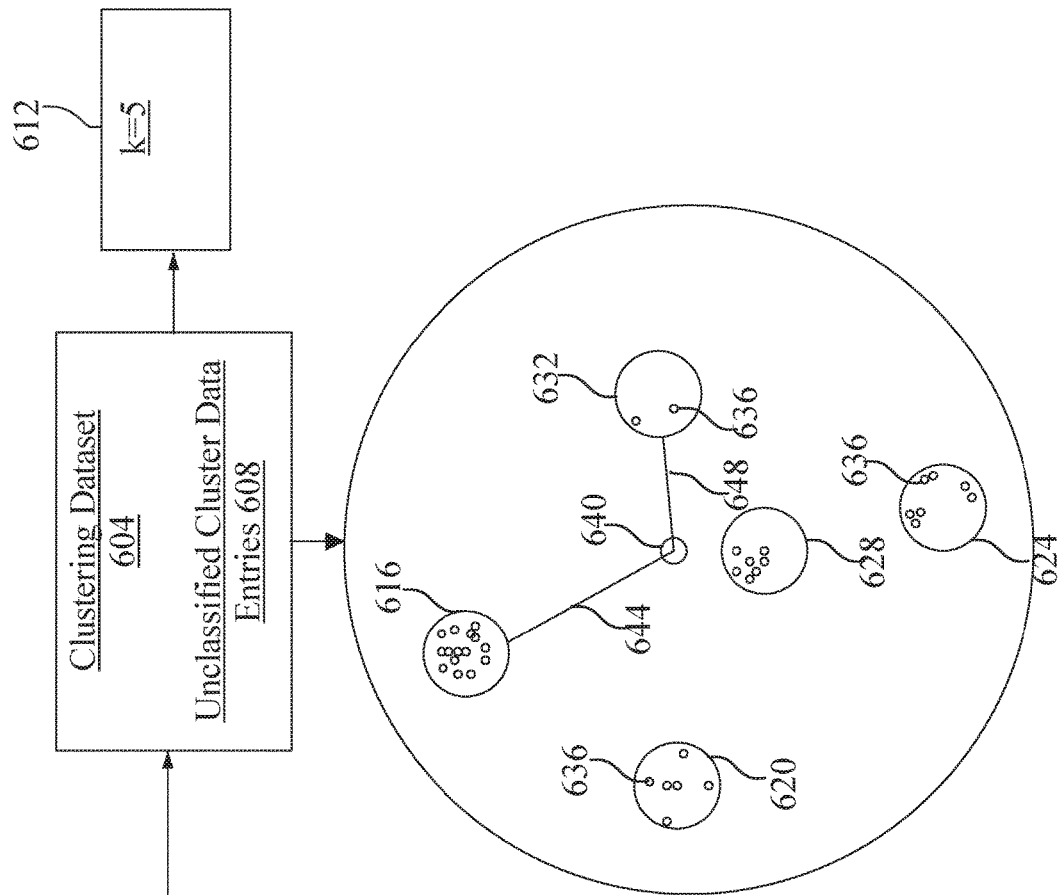
FIG. 6 is a diagrammatic representation of a k-means clustering algorithm module.

Referring now to FIG. 6, an exemplary embodiment 600 of k-means clustering algorithm 136 module is illustrated. K-means clustering algorithm 136 module receives clustering dataset 128 604 containing a plurality of unclassified cluster data entries 608 from clustering dataset 128. K-means clustering algorithm 136 module selects a k-value 612 where the k-value 612 reflects the number of classified data entry cluster 140 that will be generated by k-means clustering algorithm 136 module. K-means clustering algorithm 136 module may select a k-value 612 by classifying a therapeutic constitutional inquiry 112 as described above in more detail in reference to FIG. 1. K-means clustering algorithm 136 module may also select a k-value 612 by calculating distances from using Euclidean distance from K centroids as described above in more detail in FIG. 1. K-means clustering algorithm 136 module selects a k-value 612 of 5 and generates five classified data entry cluster 140 that include a first classified data entry cluster 140 616, a second classified data entry cluster 140 620, a third classified data entry cluster 140 624, a fourth classified data entry cluster 140 628, and a fifth classified data entry cluster 140 632. Each of the five classified data entry cluster 140 may contain one or more cluster data entries 636. In an embodiment, k-means clustering algorithm 136 module may generate a hard k-means clustering algorithm 136 wherein a cluster data entry 636 may be assigned to one classified data entry cluster 140. In such an instance, a cluster data entry 636 may only be assigned to fourth classified data entry cluster 140 628. In an embodiment, k-means clustering algorithm 136 module may generate a soft k-means clustering algorithm 136 wherein a cluster data entry 636 may be assigned to one or more classified data entry cluster 140. In such an instance, a cluster data entry 636 may be assigned to first classified data entry cluster 140 616, second classified data entry cluster 140 620, and fifth classified data entry cluster 140 632. K-means clustering algorithm 136 module calculates a degree of similarity index value that includes a measurement distance between a classified data entry cluster 140 and a user vibrancy datum 120 640. For example, k-means clustering algorithm 136 module may calculate a degree of similarity index value 644 between first classified data entry cluster 140 616 and user vibrancy datum 120 640. Similarly, k-means clustering algorithm 136 module may calculate a degree of similarity index value 648 between fifth classified data entry cluster 140 632 and user vibrancy datum 120 640. Similarity index may be calculated utilizing Euclidean distance as described above in more detail in reference to FIG. 1. In such an instance, k-means clustering algorithm 136 module may evaluate the distance and/or similarity index value between first classified data entry cluster 140 616 and user vibrancy datum 120 640 and the distance and/or similarity index value between fifth classified data entry cluster 140 632 and user vibrancy datum 120 640.

Figure 7:
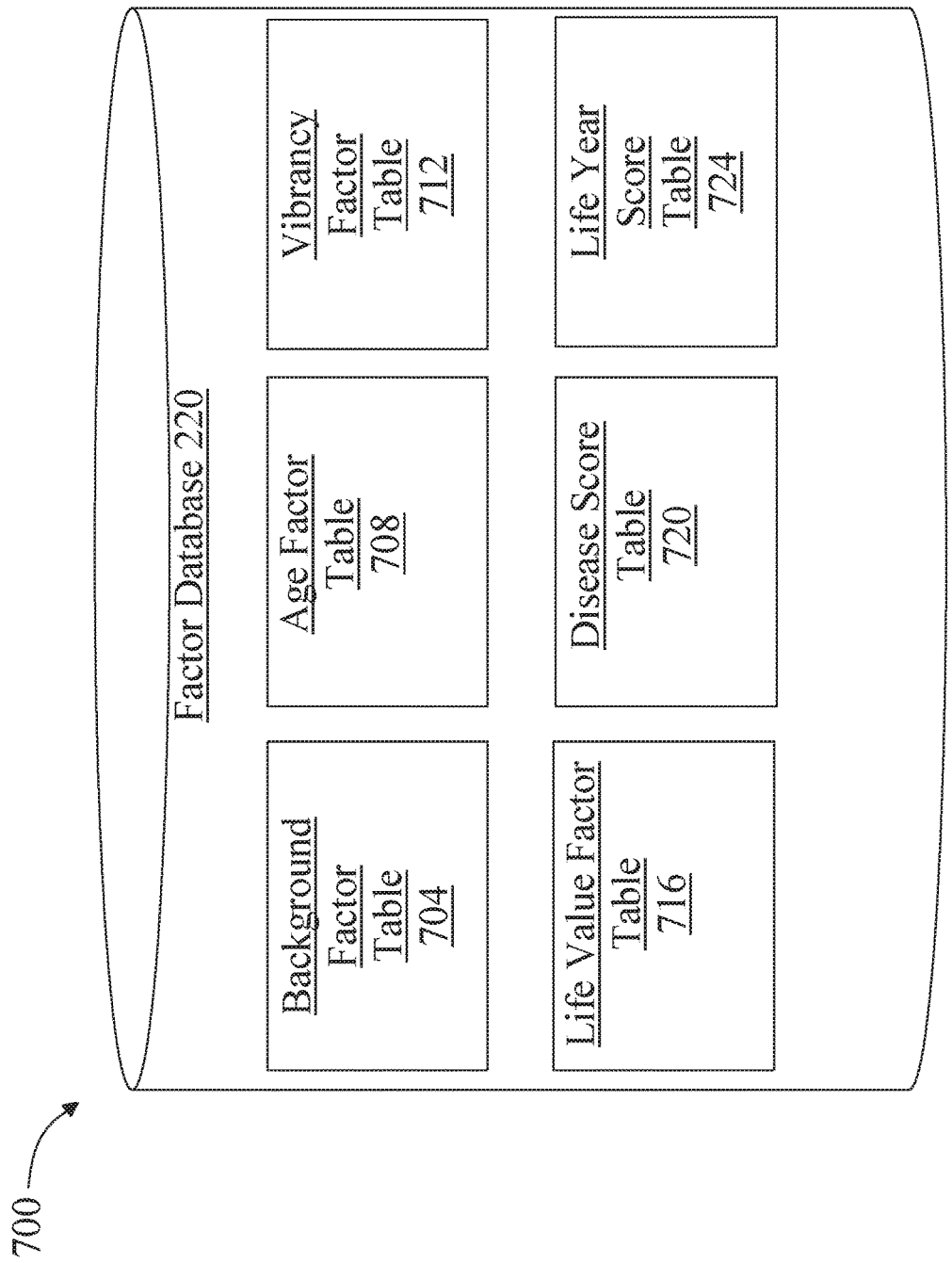
FIG. 7 is a block diagram illustrating an exemplary embodiment of a factor database.

Referring now to FIG. 7, an exemplary embodiment 700 of factor database is illustrated. Factor database may include any data structure suitable for use as vibrancy database 124. Factor database may include data utilized to calculate degree of similarity index value. One or more tables contained within factor database may include background factor table 704; background factor table 704 may include one or more data entries containing background factors. One or more tables contained within factor database may include age factor table 708; age factor table 708 may include one or more data entries containing age factors. One or more tables contained within factor database may include vibrancy factor table 712; vibrancy factor table 712 may include one or more data entries containing vibrancy factors. One or more tables contained within factor database may include life value factor table 716; life value factor table 716 may include one or more data entries containing life value factors. One or more tables contained within factor database may include disease score table 720; disease score table 720 may include one or more data entries containing disease scores. One or more tables contained within factor database may include life year score table 724; life year score table 724 may include one or more data entries containing life year scores.

Figure 8:
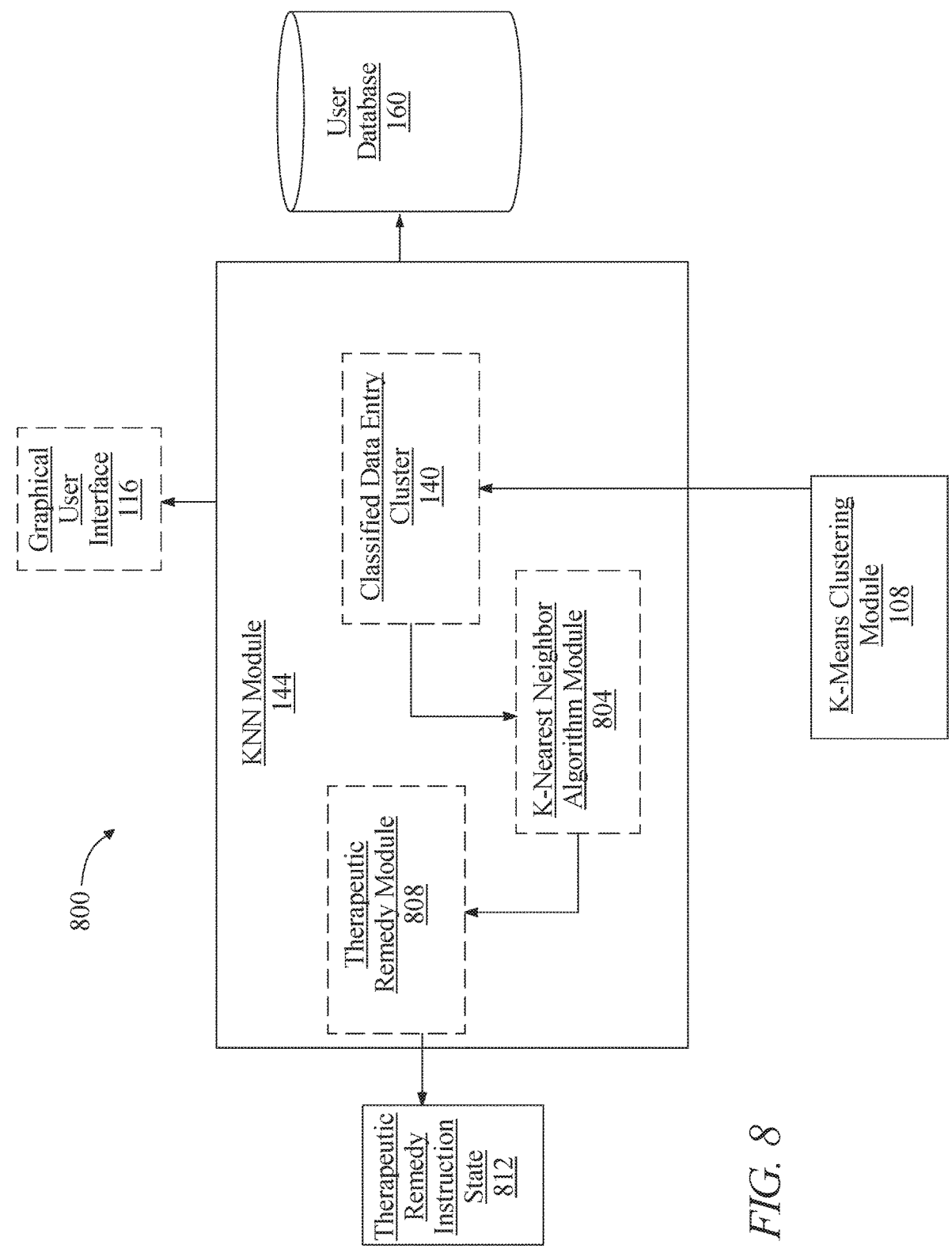
FIG. 8 is a block diagram illustrating an exemplary embodiment of a KNN module.

Referring now to FIG. 8, an exemplary embodiment of k-nearest neighbors (KNN) module is illustrated. KNN module may be implemented as a hardware or software module. KNN module is configured to receive from the K-means clustering module 108 the selected classified data entry cluster 140 and the at least a therapeutic constitutional inquiry 112; generate a k-nearest neighbors algorithm 152 utilizing the selected classified data entry cluster 140 and the at least a therapeutic constitutional inquiry 112; identify at least a therapeutic dataset contained within the selected classified data entry cluster 140 wherein the therapeutic dataset includes the at least a therapeutic constitutional inquiry 112 and a therapeutic remedy; generate a therapeutic remedy instruction set 156 as a function of identifying the therapeutic dataset; and display the therapeutic remedy instruction set 156 on a graphical user interface 116 located on the at least a computing device.

With continued reference to FIG. 8, KNN module receives classified data entry cluster 140 and therapeutic constitutional inquiry 112 selected by k-means clustering module 108. KNN module may receive classified data entry cluster 140 and therapeutic constitutional inquiry 112 utilizing any network methodology as described herein.

With continued reference to FIG. 8, KNN module may include K-nearest neighbors (KNN) algorithm module. KNN algorithm module may be implemented as a hardware or software module. KNN algorithm module generates a k-nearest neighbors algorithm 152 utilizing the selected classified data entry cluster 140 as training data and the at least a therapeutic constitutional inquiry 112. KNN algorithm module may calculate an optimal vector output for the at least a therapeutic constitutional inquiry 112 utilizing a k-nearest neighbors algorithm 152 and the selected classified data entry as training data. KNN algorithm module may modify selected classified data entry cluster 140 by representing selected classified data entry as vectors. Vectors may include mathematical representations of classified data entry cluster 140 training data. Vectors may include n-tuple of values which may represent a measurement or other quantitative value associated with a given category of data, or attribute. Vectors may be represented in n-dimensional space using an axis per category of value represented in n-tuple of values, such that a vector has a geometric direction characterizing the relative quantities of attributes in the n-tuple as compared to each other. In an embodiment, KNN module may calculate an initial heuristic ranking association between therapeutic constitutional inquiry 112 and elements of classified data entry cluster 140 training data. Initial heuristic may include selecting some number of highest-ranking associations and/or training data elements. KNN module may perform one or more processes to modify and/or format classified data entry cluster 140 training data. Classified data entry cluster 140 training data may contain "N" unique features, whereby a dataset contained within classified data entry cluster 140 training data and represented as a vector may contain a vector of length "N" whereby entry "I" of the vector represents that data point's value for feature "I." Each vector may be mathematically represented as a point in "R^N." For instance and without limitation, KNN module may modify entries contained within classified data entry cluster 140 training data to contain consistent forms of a variance. After appropriate selection of classified data entry cluster 140 training data by k-means clustering module 108, KNN module performs K-nearest neighbors algorithm 152 by classifying therapeutic datasets contained within the selected classified data entry cluster 140. Selected classified data entry cluster 140 training data may be represented as an "M×N" matrix where "M" is the number of data points contained within the classified data entry cluster 140 training data and "N" is the number of features contained within the selected classified data entry cluster 140 training data. Classifying datasets contained within selected classified data entry cluster 140 training data set may include computing a distance value between an item to be classified such as a therapeutic dataset and each dataset contained within selected classified data entry cluster 140 training set which may be represented as a vector. A value of "k" may be pre-determined or selected that will be used for classifications. In an embodiment, value of "k" may be selected as an odd number to avoid a tied outcome. In an embodiment, value of "k" may be decided by KNN module arbitrarily or value may be cross validated to find an optimal value of "k.". KNN module may then select a distance metric that will be used in K-nearest neighbors algorithm. In an embodiment, KNN module may utilize Euclidean distance which may be measure distance by subtracting the distance between a training data point and the datapoint to be classified such as therapeutic constitutional inquiry 112. In an embodiment, Euclidean distance may be calculated by a formula represented as:

$$E(x, y) = \sqrt{\sum_{i=0}^{n} (xi - yi)^2}.$$

In an embodiment, KNN module may utilize metric distance of cosine similarity which may calculate distance as the difference in direction between two vectors which may be represented as: similarity=cos θ=A×B÷∥A∥∥B∥. After selection of "k" value, and selection of distance measurement by KNN module, KNN module may partition in "R^N" into sections. Sections may be calculated using the distance metric and the available data points contained within selected classified data entry cluster 140. KNN module may calculate a plurality of optimal vector outputs; in such an instance, where a plurality of matching entries is returned, optimal vector output may be obtained by aggregating matching entries including any suitable method for aggregation, including component-wise addition followed by normalization component-wise calculation of arithmetic means, or the like.

With continued reference to FIG. 8, KNN algorithm module identifies at least a therapeutic dataset contained within the selected classified data entry cluster 140 wherein the at least a therapeutic dataset includes a therapeutic constitutional inquiry 112 and a therapeutic remedy. Therapeutic remedy may include any of the therapeutic remedies as described above in more detail in reference to FIG. 1. KNN module may include a therapeutic remedy module 808 that may be implemented as a hardware or software module. Therapeutic remedy module 808 generates a therapeutic remedy instruction set 156 as a function of identifying a therapeutic dataset. Therapeutic remedy instruction set 156 includes any of the therapeutic remedy instruction set 156 as described above in reference to FIG. 1. Therapeutic remedy instruction may include one or more therapeutic remedies selected from one or more therapeutic datasets that have been utilized to treat the same therapeutic constitutional inquiry 112. For instance and without limitation, therapeutic remedy instruction set 156 may identify a particular medication that may be utilized to treat a user with cystic fibrosis. In yet another non-limiting example, therapeutic remedy instruction set 156 may identify a particular yoga sequence that has been utilized to treat a user with generalized anxiety disorder. Therapeutic remedy instruction set 156 may be utilized to identify treatments for diseases that may impact small communities of users or that may be newly created diseases with very little medical evidence available describing how to best treat users. Identification of other users who may have been diagnosed with the same medical condition and who may have had success with a particular treatment will help best optimize treatment and inform therapeutic professionals.

With continued reference to FIG. 8, KNN module displays therapeutic remedy instruction set 156 on a graphical user interface 116 located on computing device. Therapeutic professional who entered information about a particular therapeutic constitutional inquiry 112 may be able to view therapeutic remedy instruction set 156 and be informed about ways to optimize treatment for each patient. This may also help therapeutic professionals stay active and current with new treatments that may be available as it may be difficult for them to stay active with current medical literature and research. Having a system that incorporates this information into their practice may help streamline and optimize medical treatment.

With continued reference to FIG. 8, KNN module may include a user database 160. User database 160 may be implemented as any data structure suitable for use as vibrancy database 124. User database 160 may include one or more entries regarding a user that may be utilized by KNN module to filter particular therapeutic remedies contained within therapeutic remedy instruction set 156. For example, KNN module may consult user database 160 to determine a user's allergies to medication to ensure a medication that a user is allergic to is not included in therapeutic dataset as described in more detail below.

Figure 9:
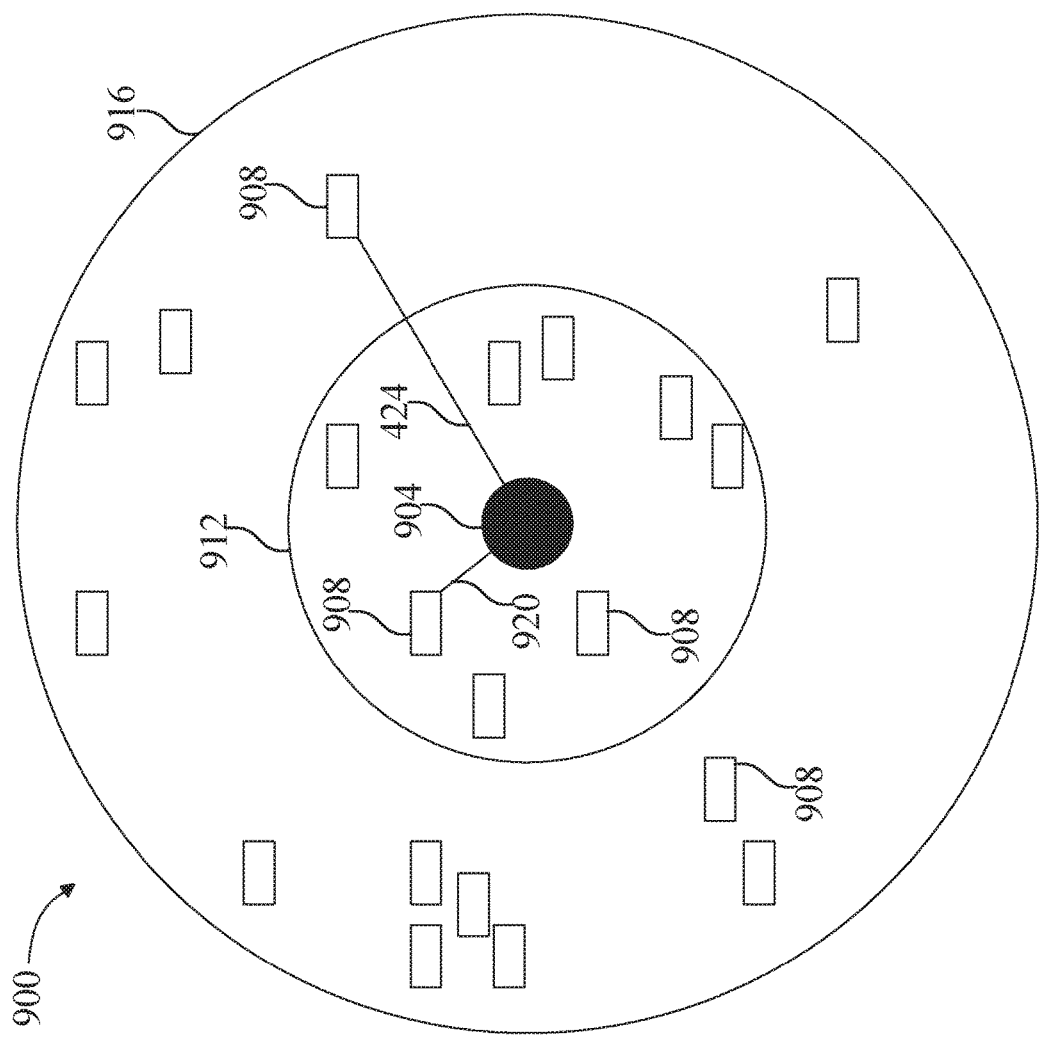
FIG. 9 is a diagrammatic representation of a K-nearest neighbors algorithm.

Referring now to FIG. 9, an exemplary embodiment 900 of k-nearest neighbors algorithm 152 is illustrated. Embodiment 904 represents a therapeutic constitutional inquiry 112 to be classified. Embodiment 908 represents data sets from selected classified data entry cluster 140. Embodiment 908 may be represented as "m" number of datasets contained within selected classified data entry cluster 140. Embodiment 912 indicates a first "k" value selected and the corresponding number of datasets contained utilizing first "k" value. Embodiment 916 indicate a second "k" value selected and the corresponding number of datasets contained utilizing second "k" value. Embodiment 920 represents distance between therapeutic constitutional inquiry 112 to be classified embodiment 904 and a particular dataset from selected classified data entry cluster 140 embodiment 908. Embodiment 920 represents distance between therapeutic constitutional inquiry 112 to be classified embodiment 904 and a particular dataset from selected classified data entry cluster 140 embodiment 908. Distance may be measured utilizing any of the methodologies as described above in reference to FIG. 1 and FIG. 8, including for example Euclidean distance and/or cosine similarity.

Figure 10:
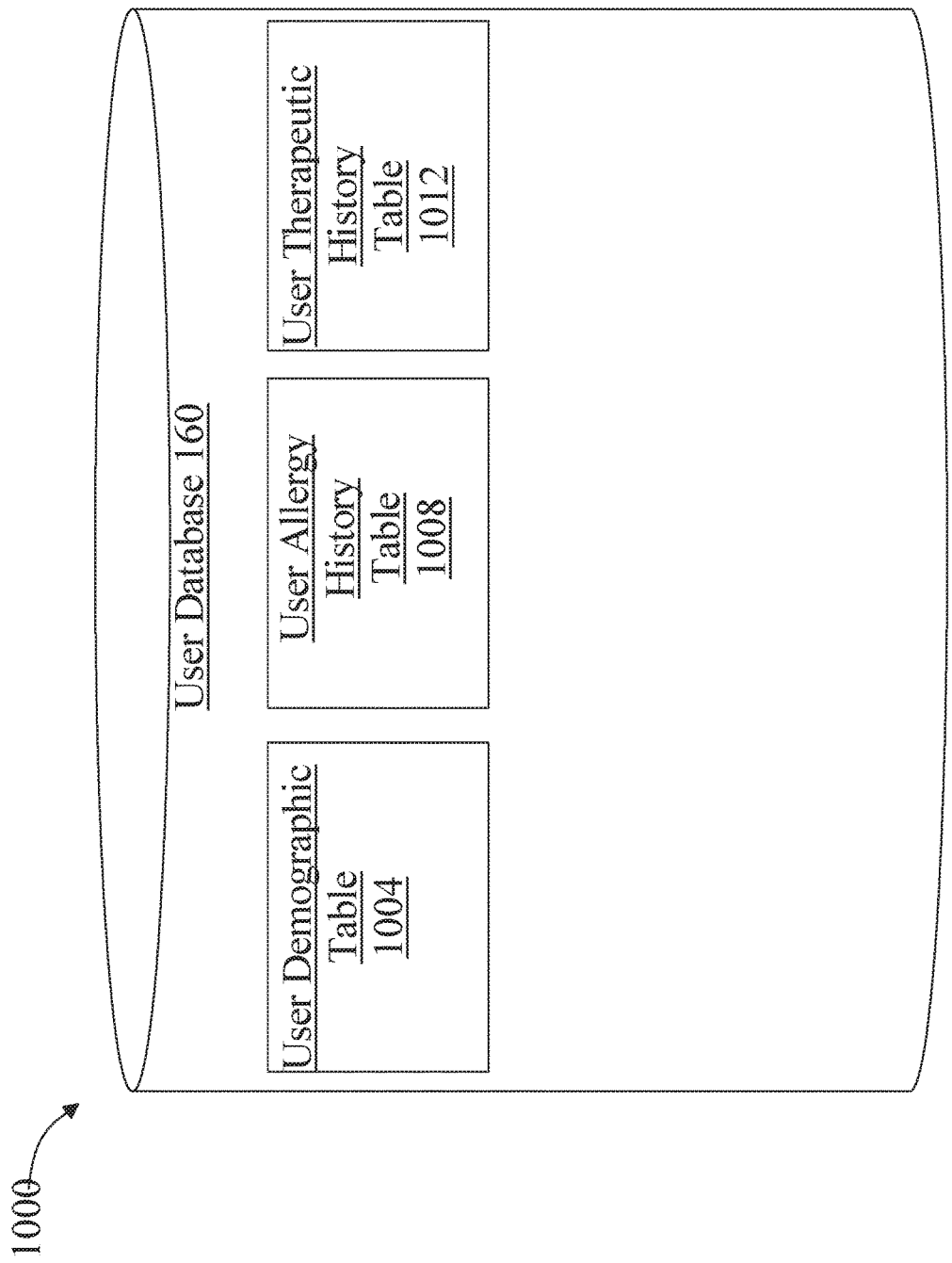
FIG. 10 is a block diagram illustrating an exemplary embodiment of a user database.

Referring now to FIG. 10, an exemplary embodiment 1000 of user database 160 is illustrated. User database 160 may be implemented as any data structure suitable for use as vibrancy database 124 as described above in more detail in reference to FIG. 1. One or more tables contained within user database 160 may include user demographic table 1004; user demographic table 1004 may include one or more data entries describing demographic information regarding a particular user. One or more tables contained within user database 160 may include user allergy history table 1008; user allergy history table 1008 may include one or more data entries describing a user's allergy history to medications, supplements, foods, chemicals, household products, and the like. One or more tables contained within user database 160 may include user therapeutic history table 1012; user therapeutic history table 1012 may include one or more data entries describing previous therapeutic remedies that a user may have utilized in the past including therapeutic remedies that were beneficial to a user and therapeutic remedies that were not beneficial to a user.

Figure 11:
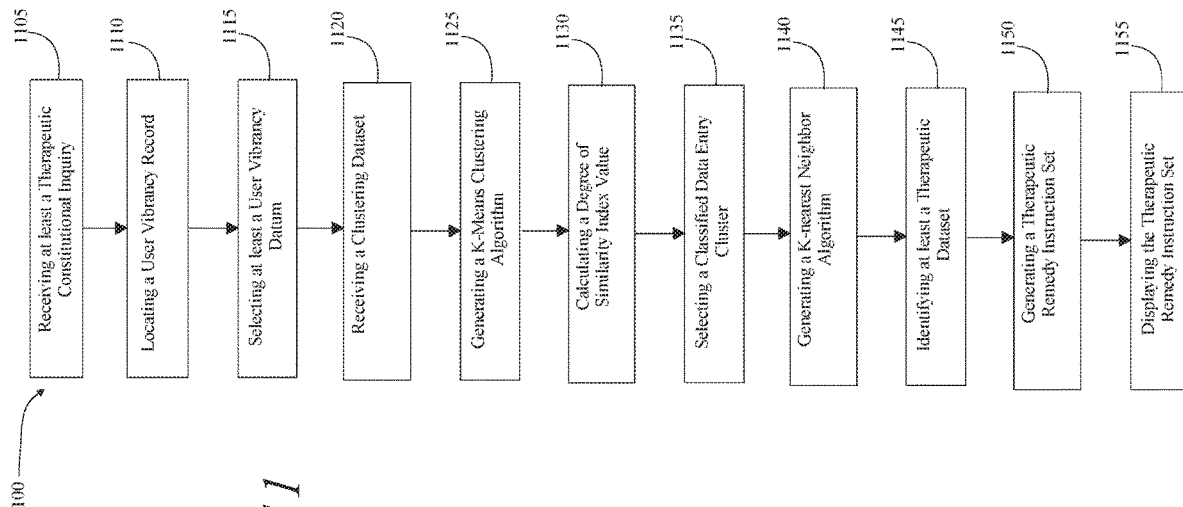
FIG. 11 is a process flow diagram illustrating an exemplary embodiment of a method of locating therapeutic remedies.

Referring now to FIG. 11, an exemplary embodiment of a method 1100 of locating therapeutic remedies is illustrated. At step 1105 at least a computing device receives at least a therapeutic constitutional inquiry 112 input from a graphical user interface 116 by a therapeutic professional. Computing device may include any of the computing devices as described herein. At least a therapeutic constitutional inquiry 112 may include any of the therapeutic constitutional inquires as described above in reference to FIGS. 1-11. In an embodiment, at least a therapeutic constitutional inquiry 112 may include a current diagnosed medical condition such as human immunodeficiency virus (HIV) or hypothyroidism. At least a therapeutic constitutional inquiry 112 includes a user identifier. User identifier may include any of the user identifiers as described above in reference to FIGS. 1-10. Graphical user interface 116 may include any of the graphical user interface 116 as described above in reference to FIGS. 1-11. In an embodiment, graphical user interface 116 may include a drop down menu where a therapeutic professional may select a therapeutic constitutional inquiry 112 from a list. In an embodiment, graphical user interface 116 may include a free form textual entry field where a therapeutic professional may type in a therapeutic constitutional inquiry 112. Therapeutic professional may include any of the therapeutic professionals as described above in reference to FIGS. 1-11. Computing device may receive at least a therapeutic constitutional inquiry 112 using any of the network methodologies as described above in reference to FIGS. 1-11.

With continued reference to FIG. 11, at step 1110 at least a computing device locates a user vibrancy record containing a plurality of user vibrancy datum 120 stored in a vibrancy database 124 as a function of the user identifier. User vibrancy record may include any of the user vibrancy records as described above in reference to FIGS. 1-11. User vibrancy record may include a plurality of user vibrancy datum 120 that may contain stored information relating to a user's medical chart including for example clinical data, lab results, immunizations, medications, and the like. User vibrancy record may be stored in vibrancy database 124 as described above in more detail in reference to FIG. 1 and FIG. 4. Computing device may locate a user vibrancy database 124 utilizing user identifier received with user constitutional inquiry. In an embodiment, at least a computing device may compare a user identifier contained within a therapeutic constitutional inquiry 112 to a user identifier located within vibrancy database 124.

With continued reference to FIG. 11, at step 1115 at least a computing device selects at least a user vibrancy datum 120 as a function of at least a therapeutic constitutional inquiry 112. At least a computing device may select at least a user vibrancy datum 120 that may be related and/or relevant to at least a therapeutic constitutional inquiry 112. For instance and without limitation, at least a computing device may select at least a user vibrancy datum 120 that includes a blood test showing elevated triglycerides for a therapeutic constitutional inquiry 112 such as stage one heart disease. In yet another non-limiting example, at least a computing device may select at least a user vibrancy datum 120 such as a genetic analysis showing a mutation to on PKD1 allele on chromosome 16 showing an increased susceptibility to develop polycystic kidney disease for a user with a therapeutic constitutional inquiry 112 that includes acute kidney disease. In an embodiment, computing device may select at least a user vibrancy datum 120 based on expert input as described above in more detail in reference to FIG. 3. In an embodiment, computing device may select at least a user vibrancy datum 120 based on learned associations between therapeutic constitutional inquiries and user vibrancy datum 120 such as by vibrancy learner 208 as described above in more detail in reference to FIG. 2.

With continued reference to FIG. 11, at step 1120 at least a computing device receives a clustering dataset 128 wherein the clustering dataset 128 includes a plurality of unclassified cluster data entries. Clustering dataset 128 may include any of the clustering dataset 128 as described above in more detail in reference to FIGS. 1-11. Clustering dataset 128 includes unclassified cluster data entries as described above in more detail in reference to FIGS. 1-11. At least a computing device receives clustering dataset 128 from clustering database 132 as described above in more detail in reference to FIG. 5. In an embodiment, clustering dataset 128 may be stored within clustering database 132 based on categorizations by demographics contained within clustering dataset 128, medical conditions contained within clustering dataset 128, vibrancy datums contained within clustering dataset 128, and/or therapeutic remedies contained within clustering dataset 128 as described above in more detail in reference to FIG. 5.

With continued reference to FIG. 11, at step 1125 at least a computing device generates a k-means clustering algorithm 136 using the clustering dataset 128 containing the plurality of cluster data entries containing unclassified data as input. K-means clustering algorithm 136 includes any of the k-means clustering algorithm 136 as described above in reference to FIGS. 1-11. K-means clustering algorithm 136 outputs a definite number of classified data entry cluster 140 wherein the classified data entry cluster 140 each contain cluster data entries. Computing device may determine k-value or definite number of classified data entry cluster 140 by evaluating therapeutic constitutional inquiry 112 to determine a constitutional classifier and selecting a definite number of classified data entry cluster 140 as a function of the constitutional classifier. In an embodiment, constitutional classifier may include classifying constitutional inquiry utilizing any of the classifiers as described above. This may include classifying constitutional inquiry by location of where a medical condition impacts a person's body or the pathology of a particular medical condition. Generating k-means clustering algorithm 136 may include generating a hard k-means clustering algorithm 136 wherein a cluster data entry is selected to be assigned to one cluster of the definite number of classified data entry cluster 140. Generating k-means clustering algorithm 136 may include generating a soft k-means clustering algorithm 136 wherein a cluster data entry is selected to be assigned to multiple clusters of the definite number of classified data entry cluster 140.

With continued reference to FIG. 11, at step 1130 at least a computing device calculates a degree of similarity index value. At least a computing device calculates a degree of similarity index value utilizing any of the methods as described above in reference to FIGS. 1-11. Degree of similarity index value includes a distance measurement between a classified data entry cluster 140ing and at least a selected user vibrancy datum 120. Distance may be measured utilizing Euclidean distance as described above in reference to FIGS. 1-11. Degree of similarity index value may include a formula that includes a background factor multiplied by an age factor and a vibrancy factor and divided by a life value factor. Disease factor may include a disease score multiplied by a life year score as described above in more detail in reference to FIG. 7. Factors utilized to calculate degree of similarity index value may be calculated utilizing any of the factors contained within factor database as described above in more detail in reference to FIG. 7.

With continued reference to FIG. 11, at step 1135 at least a computing device selects a classified data entry cluster 140 as a function of the degree of similarity index value. At least a computing device may evaluate degree of similarity calculated for each of the classified data entry cluster 140. This may be performed utilizing any of the methods as described above in reference to FIGS. 1-11.

With continued reference to FIG. 11, at step 1140 at least a computing device generates a k-nearest neighbors algorithm 152 utilizing the selected classified data entry cluster 140 and the at least a therapeutic constitutional inquiry 112. Generating k-nearest neighbors algorithm 152 may be performed utilizing any of the methodologies as described above in reference to FIGS. 1-11. Generating k-nearest neighbors algorithm 152 may include generating a first vector output containing a data entry cluster, generating a second vector output containing at least a therapeutic constitutional inquiry 112 and calculating the distance between the first vector output and the second vector output utilizing Euclidean distance measurement. This may be performed utilizing any of the methods as described above in reference to FIGS. 1-11. Generating k-nearest neighbors algorithm 152 may include generating an optimal vector output as a function of distance between a first vector output and a second vector output and identifying a therapeutic dataset utilizing the optimal vector output.

With continued reference to FIG. 11, at step 1145 at least a computing device identifies at least a therapeutic dataset contained within a selected classified data entry cluster 140 wherein the therapeutic dataset includes at least a therapeutic constitutional inquiry 112 and a therapeutic remedy. Therapeutic remedy may include any of the therapeutic remedies as described above in reference to FIGS. 1-11. Therapeutic dataset may be identified as a function of generating k-nearest neighbors algorithm.

With continued reference to FIG. 11, at least a computing device generates a therapeutic remedy instruction set 156. Therapeutic remedy instruction set 156 includes any of the therapeutic remedy instruction set 156 as described above in reference to FIGS. 1-11. Therapeutic remedy instruction set 156 may include a therapeutic remedy identified from therapeutic dataset.

With continued reference to FIG. 11, at least a computing device displays a therapeutic remedy instruction set 156 on a graphical user interface 116 located on at least a computing device. This may be performed utilizing any of the methods as described above in reference to FIGS. 1-11.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
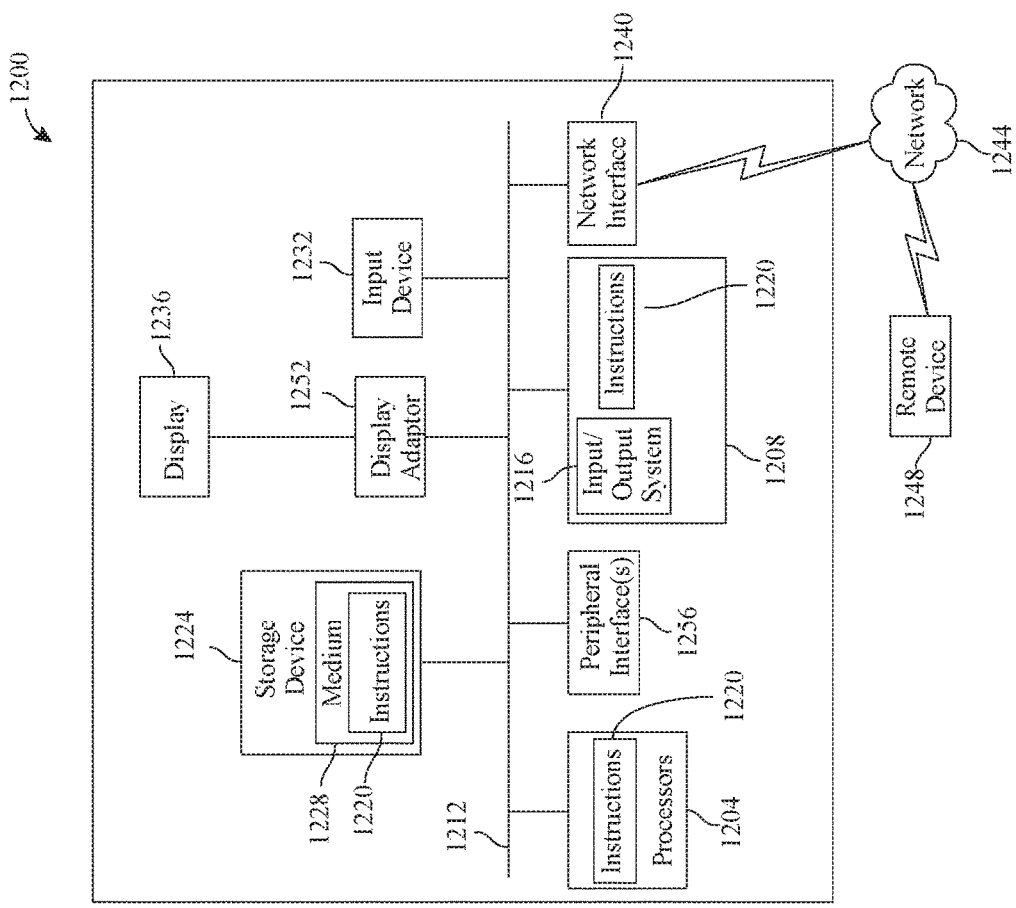
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Memory 1208 may include various components (e.g., machine-readable media) including, but not limited to, a random access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display device 1236. Examples of a display device include, but are not limited to, a liquid crystal display (LCD), a cathode ray tube (CRT), a plasma display, a light emitting diode (LED) display, and any combinations thereof. Display adapter 1252 and display device 1236 may be utilized in combination with processor 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for locating therapeutic remedies the system comprising:
   at least a computing device wherein the at least a computing device further comprises one or more network interfaces, a non-volatile memory, and one or more processors;
   a K-means clustering module operating on the at least a computing device, the k-means clustering module designed and configured to:
      receive at least a therapeutic constitutional inquiry input from a graphical user interface by a therapeutic professional wherein the at least a therapeutic constitutional inquiry includes a user identifier;
      locate a user vibrancy record containing a plurality of user vibrancy datums stored in a vibrancy database as a function of the user identifier;
      select at least a user vibrancy datum as a function of the at least a therapeutic constitutional inquiry;
      receive a clustering dataset wherein the clustering dataset further comprises a plurality of unclassified cluster data entries;
      generate a k-means clustering algorithm using the clustering dataset containing the plurality of cluster data entries containing unclassified data as input and wherein the k-means clustering algorithm outputs a definite number of classified data entry clusters wherein the classified data entry clusters each contain cluster data entries;
      generate, a machine-learning model, said machine-learning model comprising a supervised machine-learning process and trained by training data correlating classified data entry clusters to the at last a selected user vibrancy datum;
      wherein the machine-learning model is configured to receive the definite number of classified date entries and the at least a selected user vibrancy datum as an input and output a classified data entry cluster as a function of a degree of similarity index value,
      wherein said degree of similarity index value indicates a distance measurement between the classified data entry cluster and the at least a selected user vibrancy datum; and
   a K-nearest neighbors module operating on the at least a computing device the K-nearest neighbors module designed and configured to:
      receive from the K-means clustering module the selected classified data entry cluster and the at least a therapeutic constitutional inquiry;
      generate a second machine-learning model, said second machine-learning model comprising a k-nearest neighbors algorithm and trained by training data correlating the selected classified data entry cluster to the at least a therapeutic constitutional inquiry;
      wherein the second machine-learning model is configured to:
         receive the selected classified data entry cluster and the at least a therapeutic constitutional inquiry as an input and output a therapeutic remedy instruction set; and
         identify at least a therapeutic dataset contained within the selected classified data entry cluster;
      wherein said therapeutic dataset includes the at least a therapeutic constitutional inquiry and a therapeutic remedy; and
   display the therapeutic remedy instruction set on a graphical user interface located on the at least a computing device.

2. The system of claim 1, wherein generating a k-means clustering algorithm further comprises:
   evaluating the at least a therapeutic constitutional inquiry to determine a constitutional classifier; and
   selecting a definite number of classified data entry clusters as a function of the constitutional classifier.

3. The system of claim 1, wherein selecting at least a user vibrancy datum further comprises:
   categorizing the at least a user vibrancy datum to a body location; and
   selecting the at least a user vibrancy datum as a function of the body location.

4. The system of claim 1, wherein generating a k-means clustering algorithm further comprises generating a hard k-means clustering algorithm wherein a cluster data entry is selected to be assigned to one cluster of the definite number of classified data entry clusters.

5. The system of claim 1, wherein generating a k-means clustering algorithm further comprises generating a soft k-means clustering algorithm wherein a cluster data entry is selected to be assigned to multiple clusters of the definite number of classified data entry clusters.

6. The system of claim 1, wherein the degree of similarity index values includes a background factor multiplied by an age factor and by a vibrancy factor and divided by a life value factor.

7. The system of claim 6, wherein the vibrancy factor further comprises a disease score multiplied by a life year score.

8. The system of claim 1, wherein the second machine-learning model further comprises:
   generating a first vector output containing a data entry cluster;
   generating a second vector output containing the at least a therapeutic constitutional inquiry; and
   calculating the distance between the first vector output and the second vector output using Euclidean distance measurement.

9. The system of claim 8 further comprising:
   generating an optimal vector output as a function of the distance between the first vector output and the second vector output; and
   identifying the therapeutic dataset utilizing the optimal vector output.

10. A method of locating therapeutic remedies the method comprising:
   receiving by at least a computing device at least a therapeutic constitutional inquiry input from a graphical user interface by a therapeutic professional wherein the at least a therapeutic constitutional inquiry includes a user identifier;
   locating by the at least a computing device a user vibrancy record containing a plurality of user vibrancy datums stored in a vibrancy database as a function of the user identifier;
   selecting by the at least a computing device at least a user vibrancy datum as a function of the at least a therapeutic constitutional inquiry;
   receiving by the at least a computing device a clustering dataset wherein the clustering dataset further comprises a plurality of unclassified cluster data entries;
   generating by the at least a computing device a k-means clustering algorithm using the clustering dataset containing the plurality of cluster data entries containing unclassified data as input and wherein the k-means clustering algorithm outputs a definite number of classified data entry clusters wherein the classified data entry clusters each contain cluster data entries;
   generating, by the at least a computing device, a machine-learning model, said machine-learning model comprising a supervised machine-learning process and trained by training data correlating classified data entry clusters to the at last a selected user vibrancy datum;
   wherein the machine-learning model is configured to receive the definite number of classified date entries and the at least a selected user vibrancy datum as an input and output a classified data entry cluster as a function of a degree of similarity index value,
   wherein said degree of similarity index value indicates a distance measurement between the classified data entry cluster and the at least a selected user vibrancy datum;
   generating, by the at least a computing device, a second machine-learning model, said second machine-learning model comprising a k-nearest neighbors algorithm and trained by training data correlating the selected classified data entry cluster to the at least a therapeutic constitutional inquiry;
   wherein the second machine-learning model is configured to:
      receive the selected classified data entry cluster and the at least a therapeutic constitutional inquiry as an input and output a therapeutic remedy instruction set; and
      identify at least a therapeutic dataset contained within the selected classified data entry cluster;
   wherein said therapeutic dataset includes the at least a therapeutic constitutional inquiry and a therapeutic remedy; and
   displaying by the at least a computing device the therapeutic remedy instruction set on a graphical user interface located on the at least a computing device.

11. The method of claim 10, wherein generating a k-means clustering algorithm further comprises:
   evaluating the at least a therapeutic constitutional inquiry to determine a constitutional classifier; and
   selecting a definite number of classified data entry clusters as a function of the constitutional classifier.

12. The method of claim 10, wherein selecting at least a user vibrancy datum further comprises:
   categorizing the at least a user vibrancy datum to a body location; and
   selecting the at least a user vibrancy datum as a function of the body location.

13. The method of claim 10, wherein generating a k-means clustering algorithm further comprises generating a hard k-means clustering algorithm wherein a cluster data entry is selected to be assigned to one cluster of the definite number of classified data entry clusters.

14. The method of claim 10, wherein generating a k-means clustering algorithm further comprises generating a soft k-means clustering algorithm wherein a cluster data entry is selected to be assigned to multiple clusters of the definite number of classified data entry clusters.

15. The method of claim 10, wherein generating the machine-learning model further comprises calculating a degree of similarity index value wherein the degree of similarity index values includes a background factor multiplied by an age factor and by a vibrancy factor and divided by a life value factor.

16. The method of claim 10, wherein the vibrancy factor further comprises a disease score multiplied by a life year score.

17. The method of claim 10, the second machine-learning model further comprises:
   generating a first vector output containing a data entry cluster;
   generating a second vector output containing the at least a therapeutic constitutional inquiry; and
      calculating the distance between the first vector output and the second vector output using Euclidean distance measurement.
18. The method of claim 17 further comprising:
   generating an optimal vector output as a function of the distance between the first vector output and the second vector output; and
   identifying the therapeutic dataset utilizing the optimal vector output.

* * * * *